United States Patent [19]

Paioni

[11] Patent Number: 4,789,674
[45] Date of Patent: Dec. 6, 1988

[54] BI-2H-PYRROLI(DI)NEDIONES

[75] Inventor: Romeo Paioni, Riehen, Switzerland

[73] Assignee: Ciba-Geigy Corporation, Ardsley, N.Y.

[21] Appl. No.: 65,800

[22] Filed: Jun. 24, 1987

Related U.S. Application Data

[62] Division of Ser. No. 832,096, Feb. 20, 1986, abandoned.

[30] Foreign Application Priority Data

Feb. 22, 1985 [CH] Switzerland .................. 828/85

[51] Int. Cl.$^4$ .................. A61K 31/40; C07D 295/18; C07D 207/26
[52] U.S. Cl. .................. 514/227.8; 514/252; 514/333; 514/422; 514/316; 514/232.2; 544/58.5; 544/141; 544/357; 544/372; 546/256; 546/187; 548/519
[58] Field of Search .................. 544/372, 141, 58.5, 544/357; 546/256, 187; 514/252, 233, 422, 333, 234, 316; 548/519

[56] References Cited

U.S. PATENT DOCUMENTS 3,459,738  8/1969  Morren et al. .................. 260/239.3
4,144,246  6/1949  L'Italien .................. 260/326.43

FOREIGN PATENT DOCUMENTS 0007765  1/1981  Japan .................. 514/316

OTHER PUBLICATIONS

Mulholland, et al., J. Chem. Soc., Perkin Trans., 1:2121–2128, (1972).
Lee, et al., J. Am. Chem. Soc., 100:4225–4236, (1978).
Pifferi et al., Il Farmaco, 32:602–613, (1977).

Primary Examiner—Joseph Paul Brust
Attorney, Agent, or Firm—Irving M. Fishman

[57] ABSTRACT

Novel Substituted tetrahydro-, hexahydro- and octahydro-[3,4'-bi-2H-pyrrole]-2,2'-diones of the formula

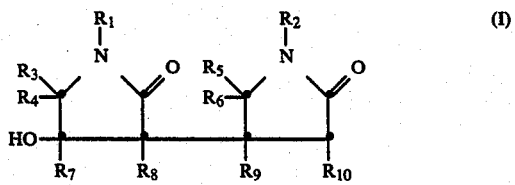

in which each of $R_1$ and $R_2$ represents a carboxy-lower alkyl radical, or an unsubstituted carbamoyl-lower alkyl radical or a carbamoyl-lower alkyl radical which is N-mono- or N,N-di-substituted by lower alkyl, hydroxy-lower alkyl, lower alkoxy-lower alkyl, amino-lower alkyl, N-mono- or N,N-di-lower alkylamino-lower alkyl, or by N,N-alkyleneamino-lower alkyl optionally substituted (in the alkyleneamino radical) by lower alkoxycarbonyl and by oxo or hydroxy, or N,N-alkenylene-amino-lower alkyl optionally substituted (in the alkenyleneamino radical) by lower alkoxycarbonyl and optionally additionally by hydroxy, or N,N-(aza-, N'-lower alkylaza- or N'-lower alkanoylaza-, oxa- or thia)alkyleneamino-lower alkyl, each of which has from 4 to 8 ring members, carbamoyl-lower alkyl, N-mono- or N,N-di-lower alkylcarbamoyl-lower alkyl, 3- to 8-membered cycloalkyl, dicycloalkyl or tricycloalkyl, or by phenyl-lower alkyl which is unsubstituted or substituted in the phenyl moiety by lower alkyl, lower alkoxy, halogen and/or trifluoromethyl, or represents a carbomoyl-lower alkyl radical which is disubstituted by alkylene optionally substituted by lower alkoxycarbonyl and by oxo or hydroxy, or by alkenylene optionally substituted by lower alkoxycarbonyl and optionally additionally by hydroxy, or by aza-, N'-lower alkylaza- or N'-lower alkanoylaza-, oxa- or thia-alkylene, each of which has from 3 to 7 chain members, each of $R_3$, $R_4$, $R_5$ and $R_6$ represents hydrogen or lower alkyl, or $R_3$ and $R_4$ together and/or $R_5$ and $R_6$ together represent a 4- to 8-membered alkylene radical, and each of $R_7$, $R_8$, $R_9$ and $R_{10}$ represents hydrogen, or $R_7$ together with $R_8$ and/or $R_9$ together with $R_{10}$ represent in each case an additional bond, and their salts, have nootropic activity and can be used as active ingredients in medicaments. They are manufactured, for example, as follows: in a compound of the formula

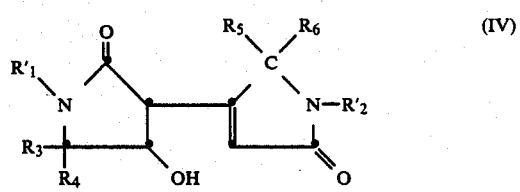

in which R'$_1$ represents a group that can be converted into a radical $R_1$ and R'$_2$ represents a radical $R_2$ or a group that can be converted into the radical $R_2$, or in a salt thereof, R'$_1$ is converted into a group $R_1$ and, optionally, a radical R'$_2$ that can be converted into $R_2$ is converted into a group $R_2$.

12 Claims, No Drawings

BI-2H-PYRROLI(DI)NEDIONES

This application is a divisional application of Ser. No. 832,096, filed Feb. 20, 1986, now abandoned.

The invention relates to novel substituted tetrahydro-, hexahydro- and octahydro-[3,4'-bi-2H-pyrrole]-2,2'-diones of the formula

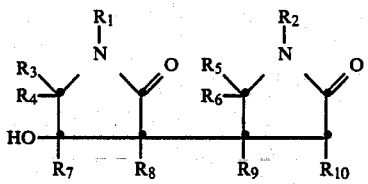

in which each of $R_1$ and $R_2$ represents a carboxy-lower alkyl radical, or an unsubstituted carbamoyl-lower alkyl radical or a carbamoyl-lower alkyl radical which is N-mono- or N,N-di-substituted by lower alkyl, hydroxy-lower alkyl, lower alkoxy-lower alkyl, amino-lower alkyl, N-mono- or N,N-di-lower alkylamino-lower alkyl, or by N,N-alkyleneamino-lower alkyl optionally substituted (in the alkyleneamino radical) by lower alkoxycarbonyl and by oxo or hydroxy, or N,N-alkenyleneamino-lower alkyl optionally substituted (in the alkenyleneamino radical) by lower alkoxycarbonyl and optionally additionally by hydroxy, or N,N-(aza-, N'-lower alkylaza- or N'-lower alkanoylaza-, oxa- or thia)alkyleneamino-lower alkyl, each of which has from 4 to 8 ring members, carbamoyl-lower alkyl, N-mono- or N,N-di-lower alkylcarbamoyl-lower alkyl, 3- to 8-membered cycloalkyl, dicycloalkyl or tricycloalkyl, or by phenyl-lower alkyl which is unsubstituted or substituted in the phenyl moiety by lower alkyl, lower alkoxy, halogen and/or trifluoromethyl, or represents a carbamoyl-lower alkyl radical which is disubstituted by alkylene optionally substituted by lower alkoxycarbonyl and by oxo or hydroxy, or alkenylene optionally substituted by lower alkoxycarbonyl and optionally additionally by hydroxy, or by aza-, N'-lower alkylaza- or N'-lower alkanoylaza-, oxa- or thia-alkylene, each of which has from 3 to 7 chain members, each of $R_3$, $R_4$, $R_5$ and $R_6$ represents hydrogen or lower alkyl, or $R_3$ and $R_4$ together and/or $R_5$ and $R_6$ together represent a 4- to 8-membered alkylene radical, and each of $R_7$, $R_8$, $R_9$ and $R_{10}$ represents hydrogen, or $R_7$ together with $R_8$ and/or $R_9$ together with $R_{10}$ represent in each case an additional bond, and their salts, especially their pharmaceutically acceptable salts.

The invention relates, for example, to 1,1',5,5'-tetrahydro-[3,4'-bi-2H-pyrrole]-2,2'-diones of formula I in which each of $R_1$ and $R_2$ represents a carboxy-lower alkyl radical, or an unsubstituted carbamoyl-lower alkyl radical or a carbamoyl-lower alkyl radical which is N-mono- or N,N-di-substituted by lower alkyl, hydroxy-lower alkyl, amino-lower alkyl, N-mono- or N,N-di-lower alkylamino-lower alkyl, 4- to 8-membered N,N-alkyleneamino- or N,N-(aza-, oxa- or thia)alkyleneamino-lower alkyl, carbamoyl-lower alkyl, N-mono- or N,N-di-lower alkylcarbamoyl-lower alkyl, 3- to 8-membered cycloalkyl, phenyl-lower alkyl which is unsubstituted or substituted in the phenyl moiety by lower alkyl, lower alkoxy, halogen and/or trifluoromethyl, or represents a carbamoyl-lower alkyl radical which is disubstituted by 3- to 7-membered alkylene or aza-, oxa- or thia-alkylene, and each of $R_3$, $R_4$, $R_5$ and $R_6$ represents hydrogen or lower alkyl, or $R_3$ and $R_4$ together and/or $R_5$ and $R_6$ together represent a 4- to 8-membered alkylene radical, and $R_7$ together with $R_8$ and $R_9$ together with $R_{10}$ represent in each case an additional bond, and their salts.

Hereinbefore and hereinafter, there are to be understood by lower radicals, for example, those having up to and including 7, especially up to and including 4, carbon atoms (C atoms). The following meanings may also be mentioned:

Lower alkyl is, for example, $C_1$–$C_4$-alkyl, such as methyl, ethyl, propyl, butyl, isobutyl, secondary butyl or tertiary butyl, but may also be $C_4$–$C_7$-alkyl, for example a pentyl, hexyl or heptyl group.

Carboxy-lower alkyl is, for example, carboxy-$C_1$–$C_4$-alkyl and denotes, for example, carboxymethyl, 2-carboxyethyl, 3-carboxypropyl or 4-carboxybutyl, but may also be 2-carboxypropyl, 2-carboxy-2-methylpropyl or 1-carboxyethyl.

Carbamoyl-lower alkyl is, for example, carbamoyl-$C_1$–$C_4$-alkyl and denotes, for example, carbamoylmethyl, 2-carbamoylethyl, 3-carbamoylpropyl or 4-carbamoylbutyl, but may also be 2-carbamoylpropyl, 2-carbamoyl-2-methylpropyl or 1-carbamoylethyl.

Hydroxy-lower alkyl carries the hydroxy group especially in a position higher than the α-position and denotes, for example, corresponding hydroxy-$C_2$–$C_4$-alkyl, such as 2-hydroxyethyl, 3- or also 2-hydroxypropyl or 4-hydroxybutyl. Carbamoyl-lower alkyl substituted by hydroxy-lower alkyl is, for example, N-(2-hydroxyethyl)carbamoylmethyl.

Lower alkoxy-lower alkyl carries the lower alkoxy group especially in a position higher than the α-position and denotes, for example, $C_1$–$C_4$-alkoxy-$C_2$–$C_4$-alkyl, such as 2-methoxyethyl, 3-methoxypropyl, and also 2-ethoxyethyl.

Amino-lower alkyl or N-mono- or N,N-di-lower alkylamino-lower alkyl carries the amino or the N-monoor N,N-di-lower alkylamino group especially in a position higher than the α-position and denotes, for example, amino-$C_1$–$C_4$-alkyl, $C_1$–$C_7$-alkylamino-$C_2$–$C_4$-alkyl or di-$C_1$–$C_4$-alkylamino-$C_2$–$C_4$-alkyl, such as 2-aminoethyl, 3-aminopropyl, 2-(N-isopropylamino)ethyl, 2-(N-tertiary butylamino)ethyl, 2-(N,Ndimethylamino)ethyl, 2-(N,N-diethylamino)ethyl or especially 2-(N,N-diisopropylamino)ethyl.

4- to 8-membered N,N-alkylene- or N,N-alkenylene- or N,N-(aza-, oxa- or thia)alkylene-amino-lower alkyl carries the N,N-disubstituted amino group especially in a position higher than the α-position and denotes, for example, 4- to 6-membered N,N-alkyleneamino-$C_2$–$C_4$-alkyl optionally substituted by lower alkoxycarbonyl, such as $C_1$–$C_4$-alkoxycarbonyl, for example methoxycarbonyl or ethoxycarbonyl, and by oxo or hydroxy, or 4- to 6-membered N,N-alkenyleneamino-$C_2$–$C_4$-alkyl optionally substituted by lower alkoxycarbonyl, such as $C_1$–$C_4$-alkoxycarbonyl, for example methoxycarbonyl or ethoxycarbonyl, and also optionally additionally substituted by hydroxy, or 4- to 6-membered N,N-(3-aza)-, N,N-(3-oxa)- or N,N-(3-thia)-alkyleneamino-$C_2$–$C_4$-alkyl, such as 2-(3,3-dimethylazetidino)ethyl, 2-pyrrolidinoethyl, 2-piperidinoethyl, 2-(3-ethoxycarbonyl-4-oxo-piperidino)ethyl, 2-(3-methoxycarbonyl-4-oxo-piperidino)ethyl, 2-(3-ethoxycarbonyl-4-hydroxypiperidino)ethyl, 2-(3-methoxycarbonyl-4 -hydroxypiperidino)ethyl, 2-(3-methoxycarbonyl-1,2,5,6-tetrahydropyridino)ethyl, 2-(2,6-dimethylpiperidino)ethyl, 2-morpholinoethyl, 2-(4-methylpiperazino)ethyl or 2-(4-acetylpiperazino)ethyl.

N-mono- or N,N-di-lower alkyl-lower alkylcarbamoyl is, for example, N-$C_1$-$C_7$-alkylcarbamoyl- or N,N-di-$C_1$-$C_4$-alkylcarbamoyl-$C_1$-$C_4$-alkyl, such as N,N-dimethylcarbamoylmethyl, N-ethylcarbamoylmethyl, N,N-diethylcarbamoylmethyl, N-(2,2-dimethylpropyl)-carbamoylmethyl, N,N-diisopropylcarbamoylmethyl, 2-(N,N-dimethylcarbamoyl)ethyl or 2-(N,N-diisopropylcarbamoyl)ethyl.

3- to 8-membered cycloalkyl, dicycloalkyl or tricycloalkyl is, for example, monocyclic $C_3$-$C_8$-cycloalkyl, such as cyclopropyl, cyclobutyl, cyclopentyl or cyclohexyl, and also cycloheptyl or cyclooctyl, bicyclic $C_7$-$C_9$-cycloalkyl, such as bicyclo-[2,2,2]-octyl, or tricyclic $C_8$-$C_{12}$-cycloalkyl, such as adamantyl.

Lower alkoxy is, for example, $C_1$-$C_4$-alkoxy, such as methoxy, ethoxy, propoxy, isopropoxy, butoxy, isobutoxy, secondary butoxy or tertiary butoxy, but may also be a $C_5$-$C_7$-alkoxy group, such as a pentyloxy, hexyloxy or heptyloxy group.

Halogen is, for example, halogen having an atomic number of up to and including 35, such as fluorine, chlorine or bromine.

Phenyl-lower alkyl is, for example, phenyl-$C_1$-$C_4$-alkyl, such as benzyl, 2-phenylethyl, 2-(3,4dimethoxyphenyl)ethyl, or 3-phenylpropyl.

3- to 7-membered alkylene denotes, for example, 3- to 7-membered alkylene which is optionally substituted by lower alkoxycarbonyl, such as $C_1$-$C_4$-alkoxycarbonyl, for example methoxycarbonyl or ethoxycarbonyl, and by oxo or hydroxy, such as 1,3-propylene, 1,3-(2,2-dimethyl)propylene, 1,4-butylene, 1,5-pentylene, 1,5-(2-methoxycarbonyl- or ethoxycarbonyl-3-oxo)pentylene, 1,5-(2-methoxycarbonyl- or 2-ethoxycarbonyl-3-hydroxy)pentylene or 1,6-heptylene. Carbamoyl-lower alkyl substituted by 3- to 7-membered alkylene thus denotes, for example, piperidinocarbonyl-lower alkyl or (3-methoxycarbonyl-4-oxo-piperidinocarbonyl)methyl, but may also be pyrrolidinocarbonylmethyl.

3- to 7-membered alkenylene denotes, for example, 1,5-(2-lower alkoxycarbonyl)pent-2-enylene or 1,5-(2-lower alkoxycarbonyl-3-hydroxy)pent-2-enylene, and correspondingly substituted carbamoyl-lower alkyl is, for example 3-$C_1$-$C_4$-alkoxycarbonyl-, such as 3-methoxycarbonyl-1,2,5,6-tetrahydro-pyridinocarbonylmethyl, or 3-$C_1$-$C_4$-alkoxycarbonyl-, such as 3-methoxycarbonyl-4-hydroxy-1,2,5,6-tetrahydro-pyridinocarbonyl-methyl.

3- to 7-membered aza-, oxa- or thia-alkylene has especially 5 or 6 chain members and denotes, for example, 1,5-(3-aza)pentylene, 1,5-(3-methyl-3-aza)-pentylene, 1,5-(3-oxa)pentylene or 1,5-(3-thia)-pentylene. Carbamoyl-lower alkyl substituted by 3- to 7-membered aza-, oxa- or thia-alkylene denotes, for example, morpholino-, (4-methyl)piperazino-, (4-acetyl)-piperazino-, or (cis-2,6-dimethyl)piperazino-carbonyl-methyl.

Depending on the number of asymmetric carbon atoms, the compounds of the formula I may occur in the form of stereoisomers, such as enantiomers or diastereoisomers, or in the form of stereoisomeric mixtures, such as enantiomeric mixtures, diastereoisomeric mixtures, racemates or mixtures of racemates. All of these correspond to the formula I and are accordingly included in the scope of the invention.

Salts of compounds of the formula I are, for example, the pharmaceutically acceptable salts thereof with bases, and also internal salts and pharmaceutically acceptable acid addition salts of compounds of the formula I in which $R_1$ and/or $R_2$ possess basic character, that is to say in which the carbamoyl group is substituted by basic radicals, such as amino-lower alkyl, N-mono- or N,N-di-lower alkylamino-lower alkyl, or N,N-alkylene- or N,N-(aza-, oxa- or thia)alkylene-amino-lower alkyl.

Pharmaceutically acceptable salts of compounds of the formula I with bases are, for example, metal salts or ammonium salts, such as alkali metal and alkaline earth metal salts, for example sodium, potassium, magnesium or calcium salts, or ammonium salts with ammonia or suitable organic amines, such as salts with aliphatic amines containing lower alkyl and/or hydroxy-lower alkyl, such as N-hydroxy-lower alkylamines, for example ethanolamine, N-hydroxy-lower alkyl-N,N-di(-lower alkyl)-amines, for example 2,2-dimethylamino-ethanol, N,N-di(hydroxy-lower alkyl)amines, for example diethanolamine, or N,N,N-tri(hydroxy-lower alkyl)-amines, for example triethanolamine, or salts with N-tri(hydroxymethyl)-methylamine, and also salts with basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, dibenzylamine or N-benzyl-$\beta$-phenylethylamine.

Pharmaceutically acceptable acid addition salts are, for example, salts with suitable mineral acids, such as hydrohalic acids, sulphuric acid or phosphoric acid, for example hydrochlorides, hydrobromides, sulphates, bisulphates or phosphates, or salts with suitable organic carboxylic or sulphonic acids, such as optionally hydroxylated aliphatic mono- or dicarboxylic acids, for example acetates, oxalates, succinates, fumarates, maleates, malates, ascorbates or citrates, with aliphatic or aromatic sulphonic acids or N-substituted sulphamic acids, for example methane-sulphonates, benzenesulphonates, p-toluenesulphonates or N-cyclohexylsulphamates.

For the purpose of isolation or purification it is also possible to use pharmaceutically unsuitable salts Only the pharmaceutically acceptable non-toxic salts are used therapeutically and these are, therefore, preferred.

The compounds of the formula I and their pharmaceutically acceptable salts possess valuable pharmacological properties, especially nootropic properties Thus, in mice, in doses of approximately 0.1 mg/kg and above i.p. and p.o., they reduce the amnesiogenic effect of an electric shock to at least the same extent as after the administration of a nootropically effective dose of piracetam (100 mg/kg i.p.). In order to demonstrate the nootropic action, the two-compartment test, for example, can be used.

There may be mentioned as literature relating to pharmacological models of this kind, for example: S. J. Sara and D. Lefevre, Psychopharmacologia 25, 32–40 (1972), Hypoxia-induced amnesia in one-trial learning and pharmacological protection by piracetam. Boggan, W. O., and Schlesinger, K., in Behavioral Biology 12, 127–134 (1974).

Furthermore, the compounds of the formula I exhibit a strong memory-improving effect in the step-down passive avoidance test according to Mondadori and Wasser, Psychopharmacology 63, 297–300 (1979). The substances are effective in the case of intraperitoneal administration 30 minutes before the learning test (effective doses 0.1, 1.0, 10 mg/kg). A marked effect could also be detected in the case of peroral administration 60 minutes before the learning test (effective doses 0.1, 1, 10 mg/kg) and in the case of intraperitoneal administration immediately after the learning test (effective doses 0.1, 1, 10 mg/kg).

The compounds of the formula I and their pharmaceutically acceptable salts can accordingly be used as nootropics, for example for the treatment of cerebral insufficiency, especially memory disorders having various causes, such as senile dementia or dementia of te Alzheimer type, and also the sequelae of brain trauma and apoplexy The invention relates especially to compounds of the formula I in which each of $R_1$ and $R_2$, independently of the other, represents carboxy-lower alkyl, carbamoyl-lower alkyl, N-mono- or N,N-di-lower alkylcarbamoyl-lower alkyl, or the following N- and N,N-substituted carbamoyl-lower alkyl radicals carrying the hydroxy, lower alkoxy, amino, lower alkylamino, di-lower alkylamino, alkylene- or alkenylene- or aza-, oxa- or thia-alkylene-amino group(s) in a position higher than the α-position with respect to the carbamoyl nitrogen atom: N-mono- or N,N-di-(hydroxy-lower alkyl)carbamoyl-lower alkyl, N-(lower alkoxy-lower alkyl)carbamoyl-lower alkyl, N-mono- or N,N-di-(amino-lower alkyl)-carbamoyl-lower alkyl, N-(lower alkylamino-lower alkyl)- or N-(di-lower alkylamino-lower alkyl)-carbamoyl-lower alkyl, or N-(alkyleneamino-lower alkyl)-carbamoyl-lower alkyl optionally substituted by lower alkoxycarbonyl and by oxo or hydroxy, or N-(alkenyleneamino-lower alkyl)carbamoyl-lower alkyl optionally substituted by lower alkoxycarbonyl and optionally additionally by hydroxy, or N-[(aza)alkyleneamino-lower alkyl]-carbamoyl-lower alkyl optionally C- and/or N'-substituted by lower alkyl or N'-substituted by lower alkanoyl, or N-[(oxa)alkyleneamino-lower alkyl]-carbamoyl-lower alkyl or N-[(thia)alkyleneamino-lower alkyl]carbamoyl-lower alkyl, each of which has from 4 to 8 ring members, or represents N-(carbamoyl-lower alkyl)carbamoyl-lower alkyl, N-(N'-mono- or N',N'-di-lower alkylcarbamoyl-lower alkyl)carbamoyl-lower alkyl, 3- to 8-membered monocyclic N-mono- or N,N-di-cycloalkylcarbamoyl-lower alkyl, N-bicycloalkylcarbamoyl-lower alkyl, N-tricycloalkylcarbamoyl-lower alkyl, or N-mono- or N,N-di-(phenyl-lower alkyl)carbamoyl-lower alkyl which is unsubstituted or substituted in the phenyl moiety by lower alkyl, lower alkoxy, halogen and/or trifluoromethyl, or N,N-alkylenecarbamoyl-lower alkyl optionally substituted by lower alkoxycarbonyl and by oxo or hydroxy, or N,N-alkenylenecarbamoyl-lower alkyl optionally substituted by lower alkoxycarbonyl and optionally additionally by hydroxy, or N,N-(aza)-alkylenecarbamoyl-lower alkyl optionally C- and/or N'-substituted by lower alkyl or N'-substituted by lower alkanoyl, or N,N-(oxa- or thia)alkylenecarbamoyl-lower alkyl, each of which has from 4 to 8 ring members, and each of $R_3$, $R_4$, $R_5$ and $R_6$ represents hydrogen or lower alkyl, or $R_3$ and $R_4$ together and/or $R_5$ and $R_6$ together represent a 4- to 8-membered alkylene radical, and each of $R_7$, $R_8$, $R_9$ and $R_{10}$ represents hydrogen, or $R_7$ together with $R_8$ and/or $R_9$ together with $R_{10}$ represent in each case an additional bond, especially those in which $R_1$ and $R_2$ are identical, $R_3$, $R_4$, $R_5$ and $R_6$ represent hydrogen and/or $R_7$ and $R_8$ and also $R_9$ and $R_{10}$ together represent in each case an additional bond, and their salts, especially their pharmaceutically acceptable salts.

The invention relates, for example, especially to compounds of the formula I in which each of $R_1$ and $R_2$, independently of the other, represents carboxy-lower alkyl, carbamoyl-lower alkyl, N-mono- or N,N-di-lower alkylcarbamoyl-lower alkyl, or the following N- and N,N-substituted carbamoyl-lower alkyl radicals carrying the hydroxy, amino, lower alkylamino, di-lower alkylamino, alkylene- or aza-, oxa- or thia-alkylene-amino group(s) in a position higher than the α-position with respect to the carbamoyl nitrogen atom: N-mono- or N,N-di-(hydroxy-lower alkyl)carbamoyl-lower alkyl, N-mono- or N,N-di(amino-lower alkyl)carbamoyl-lower alkyl, N-(lower alkylamino-lower alkyl)- or N-(di-lower alkylamino-lower alkyl)-carbamoyl-lower alkyl, or N-(alkyleneamino-lower alkyl)carbamoyl-lower alkyl, N-[(aza)alkyleneamino-lower alkyl]-carbamoyl-lower alkyl, N-[(oxa)alkyleneamino-lower alkyl]carbamoyl-lower alkyl or N-[(thia)alkyleneamino-lower alkyl]carbamoyl-lower alkyl, each of which has from 4 to 8 ring members, or represents N-(carbamoyl-lower alkyl)carbamoyl-lower alkyl, N-(N'-mono- or N',N'-di-lower alkylcarbamoyl-lower alkyl)carbamoyl-lower alkyl, 3- to 8-membered N-mono- or N,N-di-cycloalkylcarbamoyl-lower alkyl, or N-mono- or N,N-di(phenyl-lower alkyl)carbamoyl-lower alkyl which is unsubstituted or substituted in the phenyl moiety by lower alkyl, lower alkoxy, halogen and/or trifluoromethyl, or N,N-alkylene- or N,N-(aza-, oxa- or thia-)alkylene-carbamoyl-lower alkyl each having from 4 to 8 ring members, and each of $R_3$, $R_4$, $R_5$ and $R_6$ represents hydrogen or lower alkyl, or $R_3$ and $R_4$ together and/or $R_5$ and $R_6$ together represent a 4- to 8-membered alkylene radical, and $R_7$ together with $R_8$ and $R_9$ together with $R_{10}$ represent in each case an additional bond, especially those in which $R_1$ and $R_2$ are identical and $R_3$, $R_4$, $R_5$ and $R_6$ represent hydrogen, and their salts.

The invention relates above all to compounds of the formula I in which each of $R_1$ and $R_2$, independently of the other, represents carboxy-lower alkyl having a total of up to and including 5 carbon atoms, such as carboxymethyl or 2-carboxyethyl, carbamoyl-lower alkyl having a total of up to and including 5 carbon atoms, such as carbamoylmethyl or 2-carbamoylethyl, N-mono- or N,N-di-lower alkylcarbamoyl-lower alkyl each having up to and including 4 carbon atoms in each alkyl moiety, such as N-mono- or N,N-di-methylcarbamoyl-methyl or N-mono- or N,N-diisopropylcarbamoyl-methyl, N-mono- or N,N-di-(ω-hydroxy-lower alkyl)-carbamoyl-lower alkyl each having up to and including 4 carbon atoms in the hydroxyalkyl and alkyl moieties, such as N-mono- or N,N-di-(2-hydroxyethyl)carbamoylmethyl, or N-(ω-amino-lower alkyl)carbamoyl-lower alkyl having up to and including 4 carbon atoms in the amino-lower alkyl and alkyl moieties, such as N-(2-aminoethyl)carbamoylmethyl, N-[ω-(N',N'-di-lower alkylamino)-lower alkyl]carbamoyl-lower alkyl having up to and including 4 carbon atoms in each alkyl moiety, such as N-(2-dimethylaminoethyl)carbamoylmethyl or N-(2-diisopropylethyl)carbamoylmethyl, N-(ω-alkyleneamino-lower alkyl)carbamoyl-lower alkyl having from 4 up to and including 7 ring members and up to and including 4 carbon atoms in each alkyl moiety, such as N-[2-(3,3-dimethylazetidino)ethyl]carbamoylmethyl, N-(2-pyrrolidinoethyl)carbamoyl-methyl, N-(2-piperidinoethyl)carbamoylmethyl or N-[2-(2,6-dimethylpiperidino)ethyl]carbamoylmethyl, N-[ω-(3-azaalkyleneamino)-lower alkyl]carbamoyl-lower alkyl having from 4 up to and including 7 ring members and up to and including 4 carbon atoms in each alkyl moiety, such as N-(2-piperazinoethyl)carbamoylmethyl or N-[2-(4-methylpiperazino)ethyl]carbamoylmethyl, N-[ω-(3-oxaalkyleneamino)-lower alkyl]carbamoyl-lower alkyl having from 4 up to and including 7 ring members and up to and including 4 carbon atoms in each alkyl moiety, such as N-(2-morpholinoethyl)carbamoylmethyl, N-(phenyl-lower alkyl)carbamoyl-lower alkyl having up to and including 4 carbon atoms in each alkyl moiety, wherein the phenyl moiety may be mono- or di-substituted by lower alkyl having up to and including 4 carbon atoms, such as methyl, lower alkoxy having up to and including 4 carbon atoms, such as methoxy, halogen having an atomic number of up to and including 35, such as chlorine, and/or by trifluoromethyl, such as N-(2-phenylethyl)- or N-[2-(3,4-dimethoxyphenyl)ethyl]carbamoylmethyl, N-(α-carbamoyl-lower alkyl)carbamoyl-lower alkyl having up to and including 4 carbon atoms in each alkyl moiety, such as N-(carbamoylmethyl)carbamoylmethyl, N,N-alkylenecarbamoyl-lower alkyl having from 4 up to and including 7 ring members and up to and including 4 carbon atoms in the alkyl moiety, such as (3,3-dimethylazetidino)carbonylethyl, pyrrolidinocarbonylmethyl, piperidinocarbonylmethyl or (2,6-dimethylpiperidino)carbonylmethyl, N,N-(azaalkylene)-carbamoyl-lower alkyl having from 4 up to and including 7 ring members and up to and including 4 carbon atoms in the alkyl moiety, such as piperazinocarbonylmethyl or (4-methylpiperazino)carbonylmethyl, N,N-(3-oxaalkylene)carbamoyl-lower alkyl having from 4 up to and including 7 ring members and up to and including 4 carbon atoms in the alkyl moiety, such as morpholinocarbonylmethyl, or N,N-(3-thiaalkylene)carbamoyl-lower alkyl having from 4 up to and including 7 ring members and up to and including 4 carbon atoms in the alkyl moiety, such as thiomorpholinocarbonylmethyl, $R_3$, $R_4$, $R_5$ and $R_6$ represent hydrogen, or $R_3$ and $R_5$ represent identical lower alkyl radicals having up to and including 4 carbon atoms, such as methyl, an $R_4$ and $R_6$ represent hydrogen or identical lower alkyl radicals having up to and including 4 carbon atoms, such as methyl, or $R_3$ and $R_4$ together and $R_5$ and $R_6$ together represent identical lower alkylene radicals having from 2 up to and including 6 carbon atoms, such as ethylene, 1,3-propylene, 1,4-butylene, 1,5-pentylene or 1,3-(2,2-dimethyl)propylene, and $R_7$ together with $R_8$ and/or $R_9$ together with $R_{10}$ represent in each case an additional bond, especially those in which $R_1$ and $R_2$ are identical and $R_3$, $R_4$, $R_5$ and $R_6$ represent hydrogen, and their salts, especially pharmaceutically acceptable salts.

The invention relates preferably to compounds of the formula I in which $R_1$ and $R_2$ are identical and represent carboxy-$C_1$-$C_4$-alkyl, such as carboxymethyl or 2-carboxyethyl, carbamoyl-$C_1$-$C_4$-alkyl, such as carbamoylmethyl or 2-carbamoylethyl, N-mono-$C_1$-$C_7$- or N,N-di-$C_1$-$C_4$-alkylcarbamoyl-$C_1$-$C_4$-alkyl, such as N-ethyl-, N-(2,2-dimethylpropyl)- or N,N-diisopropylcarbamoylmethyl, N-(ω-di-$C_1$-$C_4$-alkylamino-$C_2$-$C_4$-alkyl)carbamoyl-$C_1$-$C_4$-alkyl, such as N-(2-diisopropylaminoethyl)carbamoylmethyl, N-(ω-hydroxy-$C_2$-$C_4$-alkyl)carbamoyl-$C_1$-$C_4$-alkyl, such as N-(2-hydroxyethyl)carbamoylmethyl, N-(ω-$C_1$-$C_4$-alkoxy-$C_2$-$C_4$-alkyl)carbamoyl-$C_1$-$C_4$-alkyl, such as N-(3-methoxypropyl)carbamoylmethyl, or N-cycloalkyl-, N-bicycloalkyl- or N-tricycloalkyl-carbamoyl-$C_1$-$C_4$-alkyl each of which is 5- or 6-membered or composed of 5- and/or 6-membered rings, such as N-cyclohexyl-, N-bicyclo[2,2,2]octyl- or adamantyl-carbamoylmethyl, 5- or 6-membered N,N-alkyleneaminocarbonyl-$C_1$-$C_4$-alkyl optionally 3-substituted by $C_1$-$C_4$-alkoxycarbonyl having up to and including 5 carbon atoms, such as methoxycarbonyl or ethoxycarbonyl, and 4-substituted by oxo or hydroxy, such as piperidinocarbonylmethyl, 3-methoxycarbonyl-4-hydroxy-piperidinocarbonyl-methyl, 3-ethoxycarbonyl-4-hydroxy-piperidinocarbonylmethyl, 3-ethoxycarbonyl-4-oxo-piperidinocarbonylmethyl or 3-methoxycarbonyl-4-oxo-prperidinocarbonylmethyl, 5- or 6-membered alkenyleneaminocarbonyl-$C_1$-$C_4$-alkyl 3-substituted by $C_1$-$C_4$-alkoxycarbonyl, such as methoxycarbonyl or ethoxycarbonyl, and optionally additionally 4-substituted by hydroxy, such as N-(3-methoxycarbonyl-1,2,5,6-tetrahydropyridino)- or N-(4-hydroxy-3-ethoxycarbonyl-1,2,5,6-tetrahydropyridino)-carbonylmethyl, 5- or 6-membered N,N-(aza)alkyleneaminocarbonyl-$C_1$-$C_4$-alkyl optionally N'-substituted by $C_1$-$C_4$-alkyl or $C_1$-$C_4$-alkanoyl, such as (N'-methyl)piperazino- or (N'-acetyl)piperazino-carbonylmethyl, 5- or 6-membered N,N-(oxa)-alkyleneaminocarbonyl-$C_1$-$C_4$-alkyl, such as morpholinocarbonylmethyl, or N-phenyl-$C_1$-$C_4$-alkylcarbamoyl-$C_1$-$C_4$-alkyl optionally mono- or di-substituted in the phenyl moiety by $C_1$-$C_4$-alkoxy, such as methoxy, such as N-(2-phenylethyl)carbamoylmethyl or N-[2-(3,4-dimethoxyphenyl)ethyl]carbamoylmethyl, $R_3$, $R_4$, $R_5$ and $R_6$ represent hydrogen and each of $R_7$, $R_8$, $R_9$ and $R_{10}$ represents hydrogen or, especially, $R_7$ together with $R_8$ and also $R_9$ together with $R_{10}$ represent in each case an additional bond, especially those in which $R_1$ and $R_2$ are identical and $R_3$, $R_4$, $R_5$ and $R_6$ represent hydrogen, and the salts, especially the pharmaceutically acceptable salts, thereof.

The invention relates first and foremost to compounds of the formula I in which $R_1$ and $R_2$ represent identical carboxy-$C_1$-$C_4$-alkyl or carbamoyl-$C_1$-$C_4$-alkyl radicals, such as carboxymethyl or carbamoylmethyl, or carbamoylmethyl radicals N-monosubstituted by ω-N,N-di-$C_1$-$C_4$-alkylamino-$C_2$-$C_4$alkyl, such as 2-diisopropylaminoethyl, or by carbamoylmethyl, N-mono- or N,N-di-substituted by ω-hydroxy-$C_2$-$C_4$-alkyl, such as 2-hydroxyethyl, or N,N-disubstituted by 4- to 6-membered (3-$C_1$-$C_4$-alkyl-3-aza)alkylene, in which $C_1$-$C_4$-alkyl represents, for example, methyl, and $R_3$, $R_4$, $R_5$ and $R_6$ represent hydrogen, and $R_7$ and $R_8$ and also $R_9$ and $R_{10}$ together in each case represent an additional bond, and the salts, especially the pharmaceutically acceptable salts, thereof.

The invention relates more especially to compounds of the formula I in which $R_1$ and $R_2$ represent identical carboxy-$C_1$-$C_4$-alkyl or carbamoyl-$C_1$-$C_4$-alkyl radicals, such as carboxymethyl or carbamoylmethyl, and $R_3$, $R_4$, $R_5$ and $R_6$ represent hydrogen, and $R_7$ and $R_8$ and also $R_9$ and $R_{10}$ together in each case represent an additional bond, and the salts, especially the pharmaceutically acceptable salts, thereof.

The invention relates to the compounds of the formula I in each case preferably in the form of their pharmaceutically acceptable alkali metal salts, alkaline earth metal salts or ammonium salts with ammonia or pharmaceutically acceptable aliphatic amines containing lower alkyl and/or hydroxy-lower alkyl, preferably in the form of their sodium, potassium, ammonium, diethylammonium, bis-(2-hydroxyethyl)ammonium, tris-(2hydroxyethyl)ammonium, tris(hydroxymethyl)methylammonium or N,N-dimethyl-N-(2-hydroxyethyl-)ammonium salts.

The invention relates specifically to the compounds of the formula I mentioned in the Examples and their pharmaceutically acceptable salts.

The invention relates also to a process, which is based on methods known per se, for the manufacture of compounds of the formula I and their salts. This process is characterised in that (a) a compound of the formula

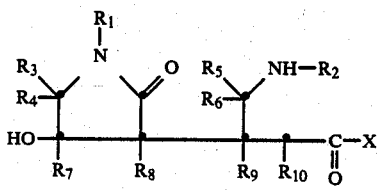
(II)

in which X represents optionally esterified or etherified hydroxy, or a salt thereof, is cyclised, or (b) in a compound of the formula

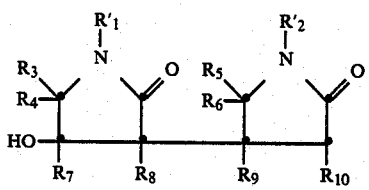
(III)

in which $R'_1$ represents a group that can be converted into a radical $R_1$ and $R'_2$ represents a radical $R_2$ or a group that can be converted into the radical $R_2$, or in a salt thereof, $R'_1$ is converted into a group $R_1$ and, optionally, a radical $R'_2$ that can be converted into $R_2$ is converted into a group $R_2$, or (c) in a compound of the formula

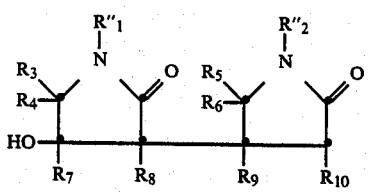
(IV)

in which $R''_1$ represents hydrogen and $R''_2$ represents hydrogen or a radical $R_2$, or in a salt thereof, the hydrogen atom $R''_1$ is replaced by a radical $R_1$ and, optionally, the hydrogen atom $R''_2$ is replaced by a radical $R_2$, or (d) a compound of the formula

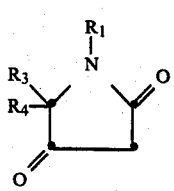
(V)

or a tautomer and/or salt thereof is condensed with a compound of the formula

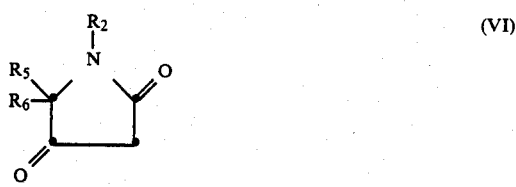
(VI)

or with a tautomer thereof, and, if desired, a compound obtainable in accordance with the process is converted into a different compound of the formula I, an isomeric mixture obtainable in accordance with the process is separated into the isomers and/or a free compound obtainable in accordance with the process is converted into a salt or a salt obtainable in accordance with the process is converted into the free compound or into a different salt.

The reactions in accordance with the process and the manufacture of novel starting materials and intermediates are carried out analogously to the manner in which known starting materials and intermediates are reacted and formed. In so doing, the appropriate customary auxiliaries, such as catalysts, condensation and solvolysis agents and/or solvents or diluents, and reaction conditions, such as temperature and pressure conditions, and also, optionally, protective gases, are used, even if this is not expressly mentioned hereinbelow.

In starting materials of the formula II for the cyclisation according to process variant (a), esterified hydroxy X is esterified, for example, by a hydrohalic acid, such as hydrochloric acid, or by a lower alkanoic acid, and etherified hydroxy is etherified, for example, by a lower alkanol or by a phenol optionally substituted, for example, by lower alkyl, lower alkoxy, halogen and/or nitro. X thus represents, for example, hydroxy, halogen, for example chlorine, lower alkanoyloxy, for example acetoxy, lower alkoxy, for example methoxy or ethoxy, phenyloxy or p-nitrophenyloxy.

Salts of compounds of the formula II are, for example, alkali metal salts, for example sodium or potassium salts, or internal salts thereof.

The intramolecular condensation is effected in customary manner: starting from compounds of the formula II in which X represents hydroxy it is effected, for example, by dehydration, that is to say removal of the water of reaction formed, for example with the aid of a water-binding agent, such as phosphorus pentoxide or an organic carbodiimide, for example dicyclohexylcarbodiimide, or by distillation, especially azeotropic distillation, starting from compounds of the formula II in which X is esterified hydroxy, it is effected, for example, in the presence of a base, such as an alkali metal or alkaline earth metal hydroxide or carbonate, for example sodium or potassium hydroxide or potassium carbonate, or a tertiary organic amine, such as a tri-lower alkylamine, for example triethylamine, or in the presence of pyridine, and, starting from compounds of the formula II in which X is etherified hydroxy, it is effected, if necessary while removing the alcohol formed, for example, by distillation or azeotropic distillation.

The starting materials of the formula II are preferably manufactured in situ and cyclised without being isolated, for example by condensing a compound of the formula

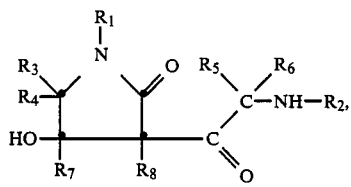 (VII)

in the presence of a base, especially a metal base, such as an alkali metal hydride, amide or alcoholate, for example sodium hydride, sodium amide, lithium diisopropylamide or a sodium or potassium lower alkoxide, above all sodium methoxide, with a compound of the formula $CH_3\text{—}C(\!=\!O)\text{-}X_1$ (VIII) in which $X_1$ represents especially etherified hydroxy, such as lower alkoxy.

If desired, in the resulting compound of the formula II in which $R_9$ and $R_{10}$ together represent an additional bond, the double bond can be saturated to form a single bond, for example by means of hydrogen in the presence of palladium-on-carbon or another suitable hydrogenation catalyst.

Intermediates of the formula VII can, in their turn, be manufactured, for example, by reacting a compound of the formula

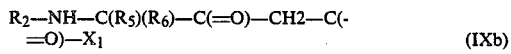

in which $X_1$ is etherified hydroxy, for example lower alkoxy, in the presence of a base, especially a metal base, such as an alkali metal hydride, amide or alcoholate, for example sodium hydride, sodium amide, lithium diisopropylamide or a sodium or potassium lower alkoxide, above all sodium methoxide, with a compound of the formula

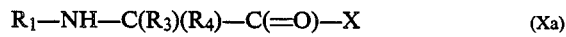

in which X is optionally esterified or etherified hydroxy, especially chlorine, lower alkoxy or optionally substituted phenyloxy, for example p-nitrophenyloxy, and, in the reaction product VII in which $R_7$ and $R_8$ together represent an additional bond, if desired saturating the double bond to form a single bond, for example by means of hydrogen in the presence of palladium-on-carbon or another suitable hydrogenation catalyst.

Compounds of the formula VII can also be obtained by reacting a compound of the formula

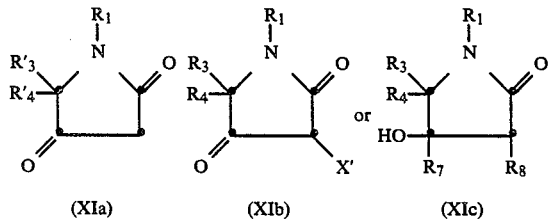

in which $R'_3$ and $R'_4$ are other than hydrogen and X' represents ethoxycarbonyl, or a tautomer, for example in each case the $\Delta$3,4-enol, of a compound XIa or XIb, in the presence of a base, especially a metal base, such as an alkali metal hydride, amide or alcoholate, for example sodium hydride, sodium amide, lithium diisopropylamide or a sodium or potassium lower alkoxide, above all sodium methoxide, with a compound of the formula $R_2\text{—}NH\text{—}C(R_5)(R_6)\text{—}C(\!=\!O)\text{-}X$ (Xb) and, in compounds VII that are obtained starting from compound XIa or XIb and in which $R_7$ and $R_8$ together represent an additional bond, if desired saturating the double bond to form a single bond, for example by means of hydrogen in the presence of palladium-on-carbon or another suitable hydrogenation catalyst.

According to process variant (b), groups $R'_1$ and $R'_2$ that can be converted into radicals $R_1$ and/or $R_2$ are, for example, functionally modified carboxy-lower alkyl radicals other than optionally substituted carbamoyl-lower alkyl $R_1$ and $R_2$, respectively, such as esterified or anhydridised carboxy-lower alkyl radicals, and also cyano-lower alkyl radicals. Esterified carboxy-lower alkyl radicals are in this case, for example, aliphatically or aromatically esterified carboxy-lower alkyl radicals, such as lower alkoxycarbonyl-lower alkyl, or phenyloxycarbonyl-lower alkyl radicals that are substituted, for example, by lower alkyl, lower alkoxy, halogen and/or by nitro, for example phenyloxy-, p-nitrophenyloxy- or 2,4-dinitrophenyloxy-carbonyl-lower alkyl radicals. Anhydridised carboxy-lower alkyl radicals are, for example, halocarbonyl-lower alkyl radicals, especially chlorocarbonyl-lower alkyl radicals. Preferably, either both radicals $R'_1$ and $R'_2$ represent identical groups that can be converted into identical radicals $R_1$ and $R_2$ or $R'_2$ represents a group $R_2$ and $R'_1$ represents a radical that can be converted into a group $R_1$.

The conversion of functionally modified carboxy-lower alkyl radicals $R'_1$ and/or $R'_2$ into carboxy-lower alkyl $R_1$ and/or $R_2$ is effected, for example, by hydrolysis, and the conversion of esterified or anhydridised carboxy-lower alkyl radicals into optionally substituted carbamoyl-lower alkyl radicals $R_1$ or $R_2$ is effected, for example, by reaction with ammonia or a corresponding amine, for example a mono- or di-lower alkylamine, mono- or di-(hydroxy-lower alkyl)amine, 4- to 8-membered N-(alkyleneamino-lower alkyl)amine optionally substituted by lower alkoxycarbonyl and by oxo or hydroxy, or N-(alkenyleneamino-lower alkyl)amine optionally substituted by lower alkoxycarbonyl and optionally additionally by hydroxy, an N-[(aza)alkyleneamino-lower alkyl]amine optionally C- and/or N'-substituted by lower alkyl or N'-substituted by lower alkanoyl, an N-[(oxa- or thia)alkyleneamino-lower alkyl]amine, or mono- or di-(cycloalkylamino-lower alkyl)amine, (bicycloalkylamino-lower alkyl)amine, (tricycloalkylamino-lower alkyl)amine each having from 3 to 8 ring members, or mono- or di-(phenyl-lower alkyl)amine optionally substituted in the phenyl moiety by lower alkyl, lower alkoxy, halogen and/or trifluoromethyl, alkyleneamine optionally substituted by lower alkoxycarbonyl and by hydroxy or oxo, alkenyleneamine optionally substituted by lower alkoxycarbonyl and optionally additionally by hydroxy, or azaalkyleneamine optionally substituted by lower alkyl and/or lower alkanoyl, or oxa- or thia-alkyleneamine, each having from 4 to 8 ring members. The hydrolysis is effected in customary manner, for example in the presence of an acidic or basic agent. The reaction of esterified or anhydridised carboxy-lower alkyl radicals with ammonia is effected, if necessary with the dehydration of initially formed ammonium salts, for example by heating, treatment with a water-binding agent, such as phosphorus pentoxide or an organic carbodiimide, for example dicyclohexylcarbodiimide, or an acid-binding agent, such as a tertiary organic nitrogen base, such as pyridine or a tri-lower alkylamine, for example triethylamine, or while removing the alcohol formed by distillation or azeotropic distillation. Using compounds of the formula III in which R'₁ and/or R'₂ represents esterified carboxy-lower alkyl as starting materials, the alcohol formed is, if necessary, removed from the reaction system by distillation or azeotropic distillation. Using compounds of the formula III in which R'₁ and/or R'₂ represents anhydridised carboxy-lower alkyl as starting materials, the reaction is advantageously carried out in the presence of a base, such as an alkali metal or alkaline earth metal hydroxide or carbonate, for example sodium or potassium hydroxide or potassium carbonate, or a tertiary organic amine, for example a tri-lower alkylamine, for example triethylamine, or in the presence of pyridine. Cyano-lower alkyl R'₁ and/or R'₂ can be hydrolysed to carboxy-lower alkyl or to carbamoyl-lower alkyl, or, by reaction with an acidic agent and then with a primary or secondary amine from among those mentioned, it can first be converted into an amidino grouping which can then be hydrolysed to the corresponding N-mono- or N,N-di-substituted carbamoyl-lower alkyl radical.

In both cases, the hydrolysis can be carried out in the presence of an acidic agent and, in the former case, also in the presence of a basic agent in the presence of hydrogen peroxide. Suitable acidic agents are, for example, mineral acids, such as hydrohalic acids, for example hydrochloric or hydrobromic acid, or oxyacids of sulphur or phosphorus, for example sulphuric acid, phosphoric acid or polyphosphoric acid. Basic agents are, for example, alkali metal or alkaline earth metal hydroxides or carbonates, for example sodium, potassium or barium hydroxide or potassium carbonate.

The starting materials of the formula III can be manufactured, for example, by reacting a compound of the formula $R'_2-NH-C(R_5)(R_6)-C(=O)-CH_2-C(=O)-X_1$ (IXc) in which $X_1$ represents etherified hydroxy, for example lower alkoxy, in the presence of a base, especially a metal base, such as an alkali metal hydride, amide or alcoholate, for example sodium hydride, sodium amide, lithium diisopropylamide or a sodium or potassium lower alkoxide, above all sodium methoxide, with a compound of the formula $R'_1-NH-C(R_3)(R_4)-C(=O)-X$ (Xb) in which X represents optionally esterified or etherified hydroxy, especially chlorine, lower alkoxy or optionally substituted phenyloxy, for example -nitrophenyloxy, and, in the reaction product of the formula

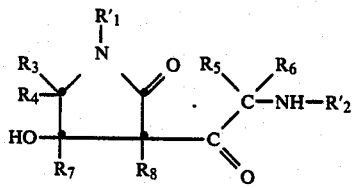
(VIIa)

in which R₇ and R₈ together represent an additional bond, if desired saturating the double bond to form a single bond, for example by means of hydrogen in the presence of palladium-on-carbon or another suitable hydrogenation catalyst, condensing the compound VIIa in the presence of a base, especially a metal base, such as an alkali metal hydride, amide or alcoholate, for example sodium hydride, sodium amide, lithium diisopropylamide or a sodium or potassium lower alkoxide, above all sodium methoxide, with a compound of the formula $CH_3-C(=O)-X_1$ (VIII) in which $X_1$ represents especially etherified hydroxy, such as lower alkoxy, and cyclising the reaction product of the formula

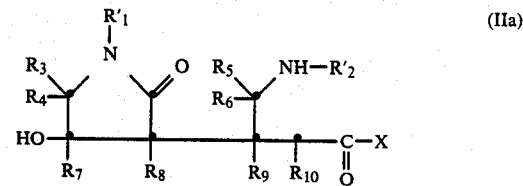
(IIa)

in which R₉ and R₁₀ together represent an additional bond, in customary manner, for example as indicated for process variant (a), and, if desired, beforehand or afterwards, hydrogenating the double bond represented by R₉ and R₁₀ together to the single bond, for example by means of hydrogen in the presence of palladium-oncarbon or another suitable hydrogenation catalyst.

An especially elegant process for the manufacture of compounds of the formula III in which R'₁ and R'₂ are identical and represent, for example, lower alkoxycarbonyl-lower alkyl, especially methoxycarbonyl-lower alkyl, and R₃, R₄, R₅ and R₆ represent hydrogen, comprises heating a compound of the formula

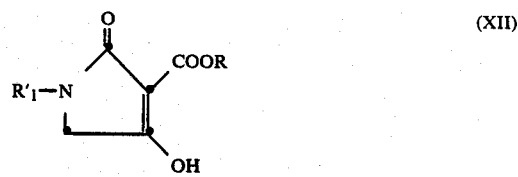
(XII)

in which COOR represents lower alkoxycarbonyl, especially methoxycarbonyl, or a tautomer, for example the corresponding Δ3,4-enol, thereof, in aqueous acetonitrile to approximately from 50° C. to 82° C., in the course of which, with the removal of the ROOC group, dimerisation to the corresponding compound of the formula

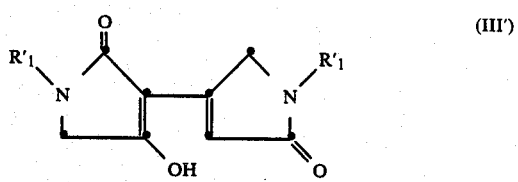
(III')

occurs, which, in an especially advantageous form of the process according to the invention, can be aminolysed by reaction with ammonia or a suitable amine to the corresponding ammonium salt of the corresponding compound of the formula

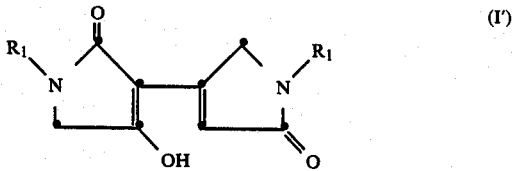
(I')

from which the free compound of the formula I' can then be freed by treatment with an acid.

The replacement of hydrogen by a radical R₁ and/or R₂ according to process variant (d) is effected, for example, by reaction with a compound of the formulae $R_1$-X (XIIIa) and/or $R_2$-X (XIIIb) in which X represents in each case reactively esterified hydroxy, such as hydroxy esterified by a hydrohalic acid or a sulphonic acid, for example chlorine, bromine or iodine or alkanesulphonyloxy or optionally substituted benzenesulphonyloxy, for example methane-, ethane-, benzene-, p-toluene- or p-bromobenzene-sulphonyloxy. In this case also, preferably, either $R''_1$ and $R_2$ both represent hydrogen or $R''_2$ is a radical $R_2$ and $R''_1$ is hydrogen.

The reaction is effected in customary manner, advantageously in the presence of a basic condensation agent, such as a metal base or a quaternary ammonium base, or a tertiary amine, for example a hydroxide, carbonate, alcoholate, amide or hydride of an alkali metal or alkaline earth metal, for example sodium or potassium hydroxide, potassium carbonate, sodium methoxide, potassium tert.-butoxide, sodium amide, lithium diisopropylamide or sodium hydride, a quaternary ammonium hydroxide, for example tetrabutylammonium hydroxide or benzyl-trimethylammonium hydroxide, or a tri-lower alkylamine or a tertiary heteroaromatic base, for example triethylamine or pyridine.

The starting materials of the formula IV can be manufactured, for example, by reacting a compound of the formula $R''_2-NH-C(R_5)(R_6)-C(=O)-CH_2-C(=O)-X_1$ (IXd) in which $X_1$ represents etherified hydroxy, for example lower alkoxy, in the presence of a base, especially a metal base, such as an alkali metal hydride, amide or alcoholate, for example sodium hydride, sodium amide, lithium diisopropylamide or a sodium or potassium lower alkoxide, above all sodium methoxide, with a compound of the formula $R''_1-NH-C(R_3)(R_4)-C(=O)-X$ (Xc) in which X is optionally esterified or etherified hydroxy, especially chlorine, lower alkoxy, or optionally substituted phenyloxy, for example p-nitrophenyloxy, and, in the reaction product of the formula

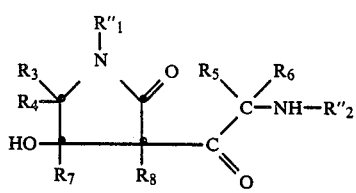

(VIIb)

in which $R_7$ and $R_8$ together represent an additional bond, if desired saturating the double bond to form a single bond, for example by means of hydrogen in the presence of palladium-on-carbon or another suitable hydrogenation catalyst, condensing the compound VIIb in the presence of a base, especially a metal base, such as an alkali metal hydride, amide or alcoholate, for example sodium hydride, sodium amide, lithium diisopropylamide or a sodium or potassium lower alkoxide, above all sodium methoxide, with a compound of the formula $CH_3-C(=O)-X_1$ (VIII) in which $X_1$ represents especially etherified hydroxy, such as lower alkoxy, and cyclising the reaction product of the formula

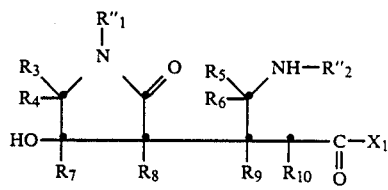

(IIb)

in which $R_9$ and $R_{10}$ together represent an additional bond, in customary manner, for example as indicated for process variant (a), and, if desired, beforehand or afterwards, hydrogenating the double bond represented by $R_9$ and $R_{10}$ together to a single bond.

Compounds of the formula IV in which $R''_1$, $R''_2$, $R_3$, $R_4$, $R_5$ and $R_6$ represent hydrogen can also be manufactured by reacting a benzoylazide which is optionally p-substituted by lower alkyl, lower alkoxy or by halogen, while irradiating with a high-pressure mercury vapour lamp, with diketene and treating the reaction product of the formula

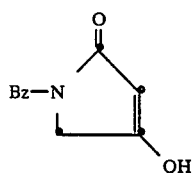

(XIV)

in which Bz represents benzoyl optionally p-substituted by lower alkyl, lower alkoxy or halogen, with a base, especially an alkali metal or alkaline earth metal hydroxide.

Compounds of the formula V in which $R''_1$ and $R''_2$ represent hydrogen and in which $R_5$ and $R_6$ have the same meanings as $R_3$ and $R_4$ can also be manufactured by reacting a compound of the formula $X_1-C(=O)-C(R_3)(R_4)-NH-C(=O)-CH_2-C(=O)-X_1$ (XV) in which the groups $X_1$ represent etherified hydroxy, for example lower alkoxy, with a metal base, for example sodium methoxide or ethoxide, and treating the resulting compound of the formula

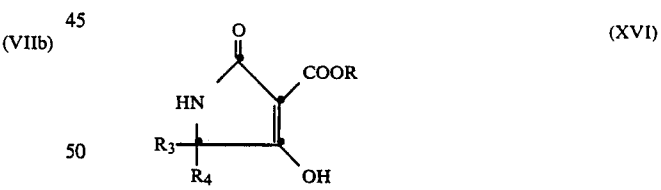

(XVI)

with a base, for example an alkali metal hydroxide, such as sodium hydroxide in water.

The condensation of compounds of the formulae V and VI according to process variant (d) generally occurs spontaneously, but is accelerated by heating and the presence of a base, such as an alkali metal or alkaline earth metal hydroxide, for example sodium, potassium or barium hydroxide, or the presence of an acid, such as a hydrohalic acid, for example hydrochloric acid, an oxyacid of sulphur or phosphorus, for example sulphuric or phosphoric acid, or an organic carboxylic acid, for example acetic acid.

In a form of process variant (d) that is especially suitable for the manufacture of compounds of the formula I in which $R_1$ and $R_2$ are identical and in which $R_5$ and $R_6$ have the same meanings as $R_3$ and $R_4$, the starting materials can be manufactured, for example, in situ and, without being isolated, subjected to autocondensation. For this, there is preferably used as starting material a compound of the formula

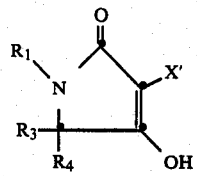

(XVII)

in which X' represents a removable radical, for example an acyl group, especially an acyl group derived from an organic carboxylic acid or from a semiester of carbonic acid, such as lower alkanoyl, for example acetyl, or benzoyl optionally substituted, for example, by lower alkyl, lower alkoxy and/or by halogen, or lower alkoxycarbonyl, for example methoxycarbonyl, and the acyl group X' is removed by heating and/or by the action of a base or an acid, the intermediately formed compound of the formula VI undergoing autocondensation in the desired manner to form the corresponding compound of the formula

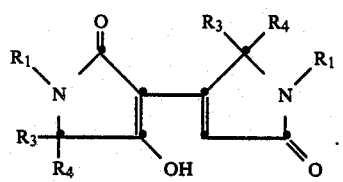

(I'')

Intermediates XVII in which X' represents an acyl group derived from a semiester of carbonic acid are manufactured, for example, as follows: a compound of the formula $R_1NH-C(R_3)(R_4)-C(=O)-X_1$ (Xa) which is obtainable by reacting compounds of the formulae $H_2N-C(R_3)(R_4)-C(=O)-X_1$ (XVIIIa) and $R_1-Y$ (XIXa) in which X represents etherified hydroxy, especially lower alkoxy, and Y represents halogen, especially chlorine or bromine, is reacted with a compound of the formula $X_2-C(=O)-CH_2-X'$ (XX) in which $X_2$ represents optionally esterified hydroxy, especially hydroxy or chlorine, and the condensation product of the formula $X'-CH_2-C(=O)-N(R_1)-C(R_3)(R_4)-C(=O)-X$ (XXI) is cyclised. The reaction of compounds (XVIIIa) and (XIXa) and of (Xa) and (XX; X=chlorine) is effected, for example, in the presence of a base, such as sodium hydroxide or a tri-lower alkylamine, for example triethylamine, and the reaction of compounds (Xa) and (XX; X=hydroxy) is effected, for example, in the presence of a water-binding agent, such as an N,N'-dialkyl- or N,N'-dicycloalkyl-carbodiimide, for example N,N'-diisopropyl- or N,N'-dicyclohexylcarbodiimide.

It is, however, also possible in a compound of the formula

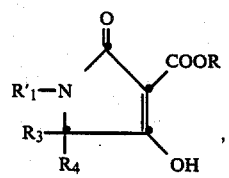

(XII)

in which COOR represents lower alkoxycarbonyl, for example methoxycarbonyl, and $R'_1$ represents lower alkoxycarbonyl-lower alkyl, for example methoxycarbonyl-lower alkyl, and which can readily be obtained, for example, by the reaction, analogous to the above-mentioned reaction cycle, of compounds (XVIIIa) and $R'_1-Y$ (XXI; Y=halogen) to form the corresponding compound $R'_1-NH-C(R_3)(R_4)-C(=O)-X_1$ (XXII), condensation thereof with a compound (XX) and cyclisation of the condensation product, to convert the group $R'_1$ in customary manner, for example as indicated under process variant (c), especially by treatment with ammonia or a corresponding amine, into a group $R_1$.

Compounds XVII in which X' represents acetyl can easily be obtained, for example, by reacting the corresponding compound (Xa) with diketene in the presence of a base, for example sodium ethoxide in ethanol.

In another preferred form of process variant (d), which also permits the manufacture of compounds of the formula I in which $R_1$ and $R_2$, or $R_3$ and $R_5$ and/or $R_4$ and $R_6$ are different, there are freed from an approximately equimolar mixture of compounds of the formulae

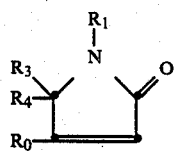

(XXIIIa)

and

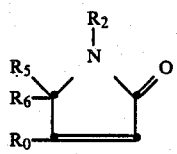

(XXIIIb)

in which the groups $R_0$ represent identical or different radicals that can be converted into hydroxy, the corresponding intermediates V and VI which condense with each other in accordance with the process under the conditions under which they are formed. If $R_1$ and $R_2$, $R_3$ and $R_5$ and/or $R_4$ and $R_6$ are different, in addition to unsymmetrical compounds I ($R_1 \neq R_2$, or $R_3 \neq R_5$, and/or $R_4 \neq R_6$), symmetrical compounds I, for example compounds of the formulae

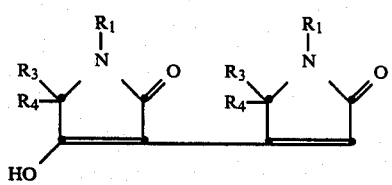

(Ia)

and

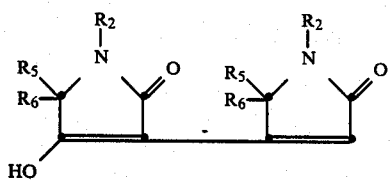

(Ib)

are also obtained which, if undesired, must be separated from the reaction mixture.

The freeing of the reactants V and VI, that is to say the conversion of $R_0$ into hydroxy, is effected in customary manner, for example by treatment with an acid. Compounds (XXIIIa) or (XXIIIb) are manufactured, for example, by converting a compound of the formula $R_3—CH(R_4)—C(=O)—CH_2—C(=O)—X_1$ (XXIVa) or $R_5—CH(R_6)—C(=O)—CH_2—C(=O)—X_1$ (XXIVb), respectively, in which $X_1$ represents etherified hydroxy, for example lower alkoxy, by reaction of a reactive ester, for example a hydrohalic ester, of an alcohol of the formula $R_0—H$ (XXV) in the presence of an alkali metal hydride, into the enol ether of the formula $R_3—CH(R_4)—C(R_0)=CH—C(=O)—X$ (XXVIa) or $R_5—CH(R_6)—C(R_0)=CH—C(=O)—X$ (XXVIb), respectively, halogenating this ether, for example by means of N-bromosuccinimide, and reacting the reaction product of the formula

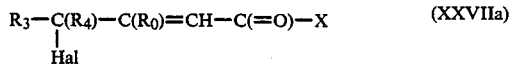
(XXVIIa)

or

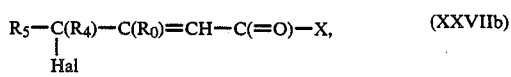
(XXVIIb)

respectively, in which Hal represents halogen, for example bromine, with the corresponding amino compound of the formula $H_2N—R_1$ (XXVIIIa) or $H_2N—R_2$ (XXVIIIb), respectively.

As conversion reactions of compounds obtainable according to the invention into other comoounds of the formula I there may be mentioned especially introduction reactions, conversion reactions and removal reactions involving the radicals $R_1$ and $R_2$ and also the saturation of double bonds, represented by $R_7$ and $R_8$ and/or $R_9$ and $R_{10}$ together.

For example, in compounds of the formula I obtainable in accordance with the process, in which $R_7$ together with $R_8$ and/or $R_9$ together with $R_{10}$ represent one or optionally two additional bond(s), the double bond or bonds can be saturated to form a single bond or single bonds, for example by means of hydrogen in the presence of a hydrogenation catalyst, for example palladium-on-carbon.

Unsubstituted carbamoyl-lower alkyl radicals $R_1$ and/or $R_2$ can, by reaction with a reactive ester, such as a hydrohalic acid ester, for example a hydrochloric, hydrobromic or hydriodic acid ester, or a sulphonic acid ester, such as a p-toluenesulphonic acid ester, of a lower alkanol, lower alkanediol, amino-lower alkanol, N-mono- or N,N-di-lower alkylaminoalkanol, N,N-alkyleneamino- or N,N-(aza-, oxa- or thia)alkyleneamino-lower alkanol, cycloalkanol, or optionally substituted phenyl-lower alkanol, also be N-mono- or N,N-di-substituted by lower alkyl, hydroxy-lower alkyl, amino-lower alkyl, N-mono- or N,N-di-lower alkylamino-lower alkyl, 4- to 8-membered N,N-alkyleneamino- or N,N-(aza-, oxa- or thia)alkyleneamino-lower alkyl, carbamoyl-lower alkyl, N-mono- or N,N-di-lower alkylcarbamoyl-lower alkyl, 3- to 8-membered cycloalkyl, or by phenyl-lower alkyl which is unsubstituted or substituted in the phenyl moiety by lower alkyl, lower alkoxy, halogen and/or trifluoromethyl. In an analogous manner, it is also possible to N,N-disubstitute a carbaxoyl-lower alkyl radical that is N-mono-substituted by one of the mentioned radicals, or to convert an unsubstituted carbamoyl-lower alkyl radical, by reaction with a reactive diester of an alkanediol or (aza-, oxa- or thia)alkanediol, into the corresponding carbamoyl-lower alkyl radical N,N-disubstituted by 3- to 7-membered alkylene or aza-, oxa- or thia-alkylene.

Optionally substituted carbamoyl-lower alkyl radicals $R_1$ and/or $R_2$ can also be hydrolysed in customary manner to carboxy-lower alkyl, for example in the presence of an acidic or basic agent. Suitable acidic agents are, for example, mineral acids, such as hydrohalic acids, for example hydrochloric or hydrobromic acid, or oxyacids of sulphur or phosphorus, for example sulphuric, phosphoric or polyphosphoric acid. Basic agents are, for example, alkali metal or alkaline earth metal hydroxides or carbonates, for example sodium, potassium or barium hydroxide or potassium carbonate.

Conversely, free carboxy-lower alkyl radicals $R_1$ and/or $R_2$ can be converted into optionally substituted carbamoyl-lower alkyl, for example by reaction with ammonia or a corresponding amine, that is to say a mono- or di-lower alkylamine, mono- or di-(hydroxy-lower alkyl)amine, 4- to 8-membered mono- or di-(N',N'-alkyleneamino-lower alkyl)-, mono- or di-[N',N'-(aza-, oxa- or thia)-alkyleneamino-lower alkyl]-amine, 3- to 8-membered mono- or di-(cycloalkylamino-lower alkyl)amine, or mono- or di-(phenyl-lower alkyl)amine optionally substituted in the phenyl moiety by lower alkyl, lower alkoxy, halogen and/or trifluoromethyl, or 4- to 8-membered alkyleneamine or aza-, oxa- or thiaalkyleneamine, if necessary with the dehydration of initially formed ammonium salts, for example by heating, treatment with a water-binding agent, such as phosphorus pentoxide or an organic carbodiimide, for example dicyclohexylcarbodiimide, or with the removal of the water formed by distillation or azeotropic distillation.

The following remarks, in particular, should be made with regard to the mentioned separation of an isomeric mixture obtainable according to the invention, or with regard to the isolation of the desired component from such a mixture:

Diastereoisomeric mixtures, for example mixtures of cis- and trans-isomers, can be separated on the basis of their differig physical properties according to the customary chemical and physico-chemical separation methods, for example by fractional crystallisation, distillation, chromatography or other phase-partitioning methods.

Enantiomeric mixtures, such as separable mixtures of the two, and optionally further, enantiomers of the same orientation of the hydrogen atoms in the 4- and 5-positions of the oxazolidine ring with respect to each other, can be separated according to customary processes for splitting racemates, for example crystallisation from an optically active solvent, chromatography over an optically active stationary or mobile phase, or intermediate formation of a diastereoisomeric auxiliary compound, for example a diastereoisomeric acid addition salt, with an optically active carboxylic or sulphonic acid, for example with the D- or L-form of tartaric acid, di-o-toluoyltartaric acid, malic acid, mandelic acid, quinic acid or a camphorsulphonic acid, separation of the diastereoisomers and freeing of the enantiomeric compound I. Preferably, the more active enantiomers are isolated in each case.

The conversion of free compounds and their salts into each other is effected, for example, by reacting a free compound with an acid, or a salt with a base or with a salt of a different acid. Salts of the novel compounds can also be used for the purification thereof and also, as mentioned, for the separation of enantiomers by converting a compound obtainable in accordance with the process into a salt, purifying this salt or separating it into the diastereoisomers, and then freeing the free compound from the salt again and, if desired, converting it into a different salt.

For example, resulting free compounds can be converted in a manner known per se into base salts, for example by reacting a solution of the free compound in a suitable solvent or solvent mixture with one of the bases mentioned hereinbefore or with a solution thereof, or with a suitable anion-exchanger.

Resulting base salts can be converted in a manner known per se into the free compounds, for example by treatment with an acid, such as a mineral acid, such as hydrochloric or sulphuric acid.

Amphoteric salts of basic compounds of the formula I can be converted into acid addition salts by treatment with an acid or into base salts by treatment with a base. An amphoteric basic compound can also be freed from one of its acid addition salts by treatment with a base or from one of its base salts by treatment with an acid.

The novel compounds, including their salts, can also be obtained in the form of the hydrates or may include the solvent used for crystallisation.

Owing to the close relationship between the novel compounds in free form and in the form of their salts, hereinbefore and hereinafter there is to be understood by the free compounds or their salts, where appropriate with regard to meaning and purpose, optionally also the corresponding salts or free compounds, respectively.

The invention relates also to those forms of the process in which a compound obtainable as an intermediate at any stage of the process is used as starting material and the remaining process steps are carried out, or in which a starting material is formed under the reaction conditions or is used in the form of a derivative, optionally a salt, thereof.

The starting materials used in the process of the present invention are preferably those which result in the compounds described at the beginning as being especially valuable. The present invention relates also to novel starting materials and to processes for the manufacture thereof.

The invention relates also to pharmaceutical preparations containing compounds of the formula I or pharmaceutically acceptable salts thereof. The preparations concerned are those for enteral, such as oral or rectal, administration and for parenteral administration to warm-blooded animals, which contain the pharmacological active ingredient on its own or together with a pharmaceutically acceptable carrier. The dosage of the active ingredient depends on the species of warm-blooded animal, the age and the individual condition and also on the mode of administration.

In a normal case, the estimated daily dose for a warm-blooded animal weighing approximately 75 kg, is, in the case of oral administration, approximately 10–100 mg, advantageously divided into several equal partial doses.

The novel pharmaceutical preparations contain, for example, from approximately 10% to approximately 80%, preferably from approximately 20% to approximately 60%, active ingredient. According to the invention, pharmaceutical preparations for enteral or parenteral administration are, for example, those in dosage unit forms, such as dragées, tablets, capsules or suppositories, and also ampoules. These are manufactured in a manner known per se, for example by means of conventional mixing, granulating, confectioning, dissolving or lyophilising processes. For example, pharmaceutical preparations for oral administration can solid carriers, if desired granulating a resulting mixture and processing the mixture or granulate, if desired or necessary, after the addition of suitable adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatine, tragacanth, methylcellulose and/or polyvinylpyrrolidone, and/or, if desired, disintegrating agents, such as the above-mentioned starches, and also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that may be resistant to gastric juices, there being used, inter alia, concentrated sugar solutions which may contain gum arabic, talc, polyvinylpyrrolidone, polyethylehe glycol and/or titanium dioxide, or lacquer solutions in suitable organic solvents or solvent mixtures or, for the manufacture of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical preparations are dry-filled capsules consisting of gelatine, and also soft sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it also being possible to add stabilisers.

Rectally administrable pharmaceutical preparations that come into consideration are, for example, suppositories which consist of a combination of the active ingredient with a suppository base. Suitable suppository bases are, for example, natural or synthetic triglycerides, paraffin hydrocarbons, polyethylene glycols or higher alkanols. It is also possible to use gelatine rectal capsules which contain a combination of the active ingredient with a base; suitable base materials are, for example, liquid triglycerides, polyethylene glycols or paraffin hydrocarbons.

Especially suitable for parenteral adminstration are aqueous solutions of an active ingredient in water-soluble form, for example in the form of a water-soluble salt, and also suspensions of the active ingredient, such as corresponding oily injection suspensions, with suitable lipophilic solvents or vehicles, such as fatty oils, for example sesame oil, or synthetic fatty acid esters, for example ethyl oleate or triglycerides, being used, or aqueous injection suspensions containing substances that increase the viscosity, for example sodium carboxymethylcellulose, sorbitol and/or dextran, and, optionally, also stabilisers.

The present invention relates also to the use of the compounds of the formula I and the salts of such compounds having salt-forming properties, preferably for the treatment of cerebral insufficiency.

The following Examples illustrate the invention described above; they are not, however, intended to limit the scope thereof in any way. Temperatures are given in degrees Celsius and pressures in mbar.

EXAMPLE 1

9.7 g (0.03 mol) of 1,1',5,5'-tetrahydro-4-hydroxy-2,2'-dioxo-[3,4'-bi-2H-pyrrole]-1,1'-diacetic acid dimethyl ester are dissolved in 100 ml of a concentrated aqueous ammonia solution and stirred at room temperature for 12 hours. The reddish-brown solution is then concentrated to dryness by evaporation under a water-jet vacuum. The resulting residue is taken up in 200 ml of water, and a concentrated aqueous solution of hydrochloric acid is added until a strongly acidic reaction takes place. The resulting colourless precipitate is filtered off, washed with water and acetone and dried under a high vacuum at 50°. 1,1',5,5'-tetrahydro-4-hydroxy-2,2'-dioxo-[3,4'-bi-2H-pyrrole]diacetic acid diamide is obtained in the form of white microcrystals having a melting point of 298°–300° (decomposition).

The 1,1',5,5'-tetrahydro-4-hydroxy-2,2'-dioxo-[3,4'-bi-2H-pyrrole]-1,1'-diacetic acid dimethyl ester used as starting material can be manufactured as follows:

(a) 197.6 g (1 mol) of iminodiacetic acid dimethyl ester hydrochloride are suspended in 1000 ml of chloroform and cooled to 0°. At this temperature, first of all 222.6 g (2.2 mol) of triethylamine are added dropwise over a period of 10 minutes and then a solution of 150.2 g (1.1 mol) of malonic acid monomethyl ester chloride in 120 ml of chloroform is added dropwise over a period of 90 minutes. The reaction mixture is then stirred at room temperature for 4 hours and then 500 ml of water are added. The organic phase is separated off and washed in succession with 500 ml in each case of 2N hydrochloric acid, water, saturated sodium bicarbonate solution and again water, dried over magnesium sulphate, filtered and concentrated to dryness by evaporation in vacuo. The oily residue is crystallised by the addition of 400 ml of hexane while stirring. After filtration, washing with a small quantity of hexane and drying in vacuo there are obtained colourless crystals, melting point 61°–62°, of N-(2-methoxycarbonylacetyl)-iminodiacetic acid dimethyl ester.

(b) 196.5 g (0.75 mol) of N-(2-methoxycarbonylacetyl)iminodiacetic acid dimethyl ester dissolved in 200 ml of methanol are added dropwise to a solution of 17.1 g of sodium (0.75 mol) in 900 ml of methanol. The reaction mixture is then heated under reflux for 12 hours, cooled to room temperature and concentrated to dryness by evaporation under a water-jet vacuum. The yellowish residue is dissolved in 500 ml of water, filtered over a layer of diatomaceous earth and then 160 ml of semi-concentrated aqueous hydrochloric acid are added. After stirring for a further one hour the resulting crystals are filtered off, washed with acetone and dried. 2,5-dihydro-4-hydroxy-3-methoxycarbonyl-2-oxo-1H-pyrrole-1-acetic acid methyl ester is obtained having a melting point of 192° (decomposition).

(c) 75.5 g (0.165 mol) of the above-described pyrrole derivative are suspended in 75 ml of water and 750 ml of acetonitrile. Heating to 65°–70°, while stirring, initiates the removal of carbon dioxide and a clear solution is formed which, after 30 minutes, is concentrated by evaporation under a water-jet vacuum. The oily residue is taken up in 500 ml of water and heated to 90°–95°. The resulting product is filtered off, washed with water and dried under a high vacuum. 1,1',5,5'-tetrahydro-4-hydroxy-2,2'-dioxo-[3,4'-bi-2H-pyrrole] -1,1'-diacetic acid dimethyl ester is obtained in the form of colourless crystals having a melting point of 228° (decomposition).

EXAMPLE 2

6.5 g (0.02 mol) of 1,1',5,5'-tetrahydro-4-hydroxy-2,2'-dioxo-[3,4'-bi-2H-pyrrole]-1,1'-diacetic acid dimethyl ester are stirred in 30 ml of 2-phenylethylamine for 12 hours at 110°. The suspension that gradually forms is then cooled to room temperature, poured onto 250 ml of water, rendered strongly acidic with a concentrated aqueous hydrochloric acid solution and filtered with suction. The filtration residue is washed several times with water, briefly stirred in 150 ml of acetone at boiling temperature, cooled, filtered off and dried under a high vacuum. 1,1',5,5'-tetrahydro-4-hydroxy-2,2'-dioxo-[3,4'-bi-2H-pyrrole]-1,1'-di-N-(2-phenylethyl)-amide is obtained in the form of white microcrystals having a melting point of 250° (decomposition).

EXAMPLE 3

6.5 g (0.02 mol) of 1,1',5,5'-tetrahydro-4-hydroxy-2,2'-dioxo-[3,4'-bi-2H-pyrrole]-1,1'-diacetic acid dimethyl ester are stirred in 100 ml of water and 20 ml of concentrated aqueous sodium hydroxide solution for 12 hours at 90°. The solution is then rendered strongly acidic with concentrated aqueous hydrochloric acid solution while cooling with an ice-water bath. The resulting suspension is stirred for a further 2 hours in order to complete the reaction, then filtered, washed with water and acetone and dried under a high vacuum. 1,1',5,5'-tetrahydro-4-hydroxy-2,2'-dioxo-[3,4'-bi-2H-pyrrole]-1,1'-diacetic acid is obtained in the form of white microcrystals having a melting point of 268° (decomposition).

EXAMPLE 4

4.9 g (0.015 mol) of 1,1',5,5'-tetrahydro-4-hydroxy-2,2'-dioxo-[3,4'-bi-2H-pyrrole]-1,1'-diacetic acid dimethyl ester are heated in 30 ml of 2-diisopropylaminoethylamine for 12 hours at 105°. The reaction mixture is cooled and concentrated under a water-jet vacuum. The oily residue is taken up in 150 ml of diethyl ether and rendered strongly acidic with an excess of an ethereal hydrochloric acid solution (approximately 4N). The solution, in which a resinous precipitate forms, is again concentrated under a water-jet vacuum. The hygroscopic residue is dissolved in 100 ml of water, and the solution is rendered alkaline with 2N sodium hydroxide solution, and 100 ml of diethyl ether are added. After separation of the aqueous phase, white crystals are deposited in the ethereal phase which are filtered off and dried in vacuo. The 2-diisopropylaminoethylammonium salt of 1,1',5,5'-tetrahydro-4-hydroxy-2,2'-dioxo-[3,4'-bi-2H-pyrrole]-1,1'-diacetic acid di-N-(2-diisopropylaminoethyl)-amide is obtained in the form of colourless crystals having a melting point of 163°–164°.

EXAMPLE 5

Analogously to the procedure described in Example 2, from 4.8 g (0.015 mol) of 1,1',5,5'-tetrahydro-4-hydroxy-2,2'-dioxo-[3,4'-bi-2H-pyrrole]-1,1'-diacetic acid dimethyl ester and 25 ml of piperidine there is obtained 1,1',5,5'-tetrahydro-4-hydroxy-2,2'-dioxo-[3,4'-bi-2H-pyrrole]-1,1'-diacetic acid dipiperidide in the form of pale yellow microcrystals having a melting point of 150°–155° (decomposition).

EXAMPLE 6

Analogously to the procedure described in Example 1, from 4.8 g (0.015 mol) of 1,1',5,5'-tetrahydro-4-hydroxy-2,2'-dioxo-[3,4'-bi-2H-pyrrole]-1,1'-diacetic acid dimethyl ester and 25 ml of cyclohexylamine there is obtained 1,1',5,5'-tetrahydro-4-hydroxy-2,2'-dioxo-[3,4'-bi-2H-pyrrole]-1,1'-diacetic acid di-N-cyclohexylamide in the form of white crystals having a melting point of 257° (decomposition).

EXAMPLE 7

Analogously to the procedure described in Example 2, from 4.8 g (0.015 mol) of 1,1',5,5'-tetrahydro-4-hydroxy-2,2'-dioxo-[3,4'-bi-2H-pyrrole]-1,1'-diacetic acid dimethyl ester and 25 ml of morpholine there is obtained 1,1',5,5'-tetrahydro-4-hydroxy-2,2'-dioxo-[3,4'-bi-2H-pyrrole]-1,1'-diacetic acid dimorpholide in the form of pale yellow crystals having a melting point of 250° (decomposition).

EXAMPLE 8

Analogously to the procedure described in Example 2, from 6.4 g (0.02 mol) of 1,1',5,5'-tetrahydro-4-hydroxy-2,2'-dioxo-[3,4'-bi-2H-pyrrole]-1,1'-diacetic acid dimethyl ester and 50 ml of a 70% aqueous ethylamine solution there is obtained, after stirring for 48 hours at room temperature, 1,1',5,5'-tetrahydro-4-hydroxy-2,2'-dioxo-[3,4'-bi-2H-pyrrole]-1,1'-diacetic acid di-N-ethylamide in the form of pale yellow crystals having a melting point of 190° (decomposition).

EXAMPLE 9

Analogously to the procedure described in Example 2, from 4.8 g (0.015 mol) of 1,1',5,5'-tetrahydro-4-hydroxy-2,2' -dioxo-[3,4'-bi-2H-pyrrole]-1,1'-diacetic acid dimethyl ester and 20 ml of 2-(3,4-dimethoxyphenyl)-ethylamine there is obtained 1,1',5,5'-tetrahydro-4-hydroxy-2,2'-dioxo-[3,4'-bi-2H-pyrrole]-1,1'-diacetic acid di-N-[2-(3,4-dimethoxyphenyl)-ethyl]-amide in the form of white microcrystals having a melting point of 199° (decomposition).

EXAMPLE 10

Analogously to the procedure described in Example 2, from 4.8 g (0.015 mol) of 1,1',5,5'-tetrahydro-4-hydroxy-2,2'-dioxo-[3,4'-bi-2H-pyrrole]-1,1'-diacetic acid diethyl ester and 12 ml of 2,2-dimethylpropylamine there is obtained 1,1',5,5'-tetrahydro-4-hydroxy-2,2'-dioxo-[3,4'-bi-2H-pyrrole]-1,1'-diacetic acid di-N-(2,2-dimethylpropyl)-amide in the form of white microcrystals having a melting point of 242° (decomposition).

EXAMPLE 11

Analogously to the procedure described in Example 2, from 4.8 g (0.015 mol) of 1,1',5,5'-tetrahydro-4-hydroxy-2,2'-dioxo-[3,4'-bi-2H-pyrrole]-1,1'-diacetic acid diethyl ester and 40 ml of a 70% aqueous solution of 3-methoxypropylamine there is obtained, after stirring for 48 hours at room temperature, 1,1',5,5'-tetrahydro-4-hydroxy-2,2'-dioxo-[3,4'-bi-2H-pyrrole]-1,1'-diacetic acid di-N-(3-methoxypropyl)-amide in the form of pale yellowish microcrystals having a melting point of 214° (decomposition).

EXAMPLE 12

4.9 g (0.015 mol) of 1,1',5,5'-tetrahydro-4-hydroxy-2,2'-dioxo-[3,4'-bi-2H-pyrrole]-1,1'-diacetic acid dimethyl ester are stirred in 40 ml of a 70% aqueous solution of 2-(N-methylamino)-ethanol for 48 hours at room temperature. The reaction mixture is concentrated by evaporation under a high vacuum and the oily residue is taken up in 20 ml of methanol, and 5 ml of a 30% sodium methoxide solution are added. The addition of 200 ml of acetone causes the sodium salt of 1,1',5,5'-tetrahydro-4-hydroxy-2,2'-dioxo-[3,4'-bi-2H-pyrrole]-1,1'-diacetic acid di-N-methyl-N-(2-hydroxyethyl)-amide to crystallise out. After filtration, washing and drying under a high vacuum, this salt is obtained in the form of pale light-brown microcrystals having a melting point of 158° (decomposition).

EXAMPLE 13

2.9 g (0.01 mol) of 1,1',5,5'-tetrahydro-4-hydroxy-2,2'-dioxo-[3,4'-bi-2H-pyrrole]-1,1'-diacetic acid diamide are suspended in 50 ml of water and, at room temperature, 2 ml of a concentrated aqueous ammonia solution are added. The resulting yellowish solution is concentrated to dryness by evaporation under a water-jet vacuum and the amorphous residue is taken up in 30 ml of acetone and filtered, and the filtration residue is then washed with acetone and dried under a high vacuum. The ammonium salt of 1,1',5,5'-tetrahydro-4-hydroxy-2,2'-dioxo-[3,4'-bi-2H-pyrrole]-1,1'-diacetic acid diamide is obtained in the form of a pale yellowish powder; melting point 133° (decomposition).

EXAMPLE 14

In a manner analogous to that described in Example 13, from 2.9 g (0.01 mol) of 1,1',5,5'-tetrahydro-4-hydroxy-2,2'-dioxo-[3,4'-bi-2H-pyrrole]-1,1'-diacetic acid diamide and 0.1N aqueous sodium hydroxide solution (added until pH 6.4 is obtained) there is obtained the sodium salt of 1,1',5,5'-tetrahydro-4-hydroxy-2,2'-dioxo-[3,4'-bi-2H-pyrrole]-1,1'-diacetic acid diamide in the form of a white powder; melting point 150° (decomposition).

EXAMPLE 15

In a manner analogous to that described in Example 13, from 2.9 g (0.01 mol) of 1,1',5,5'-tetrahydro-4-hydroxy-2,2'-dioxo-[3,4'-bi-2H-pyrrole]-1,1'-diacetic acid diamide and an aqueous diethanolamine solution (added until pH 6.5 is obtained) there is obtained the diethanolammonium salt of 1,1',5,5'-tetrahydro-4-hydroxy-2,2'-dioxo-[3,4'-bi-2H-pyrrole]-1,1'-diacetic acid diamide in the form of a white powder; melting point 130° (decomposition).

EXAMPLE 16

In a manner analogous to that described in Example 13, from 1,1',5,5'-tetrahydro-4-hydroxy-2,2'-dioxo-[3,4'-bi-2H-pyrrole]-1,1'-diacetic acid diamide and 5 ml of 2-dimethylaminoethanol there is obtained the N,N- dimethyl-N-ethanolammonium salt of 1,1′,5,5′-tetrahydro-4-hydroxy-2,2′-dioxo-[3,4′-bi-2H-pyrrole]-1,1′-diacetic acid diamide in the form of a white powder; melting point 170° (decomposition).

EXAMPLE 17

2.1 g (0.007 mol) of 1,1′,5,5′-tetrahydro-4-hydroxy-2,2′-dioxo-[3,4′-bi-2H-pyrrole]-1,1′-diacetic acid are suspended in 30 ml of methanol and, at room temperature, 6 ml of a 30% sodium methoxide solution in ethanol are added. After stirring for 3 hours a small quantity of undissolved material is filtered off and 50 ml of diethyl ether are added to the filtrate. The crystals that are formed are filtered off, washed briefly with an ether/methanol mixture (2:1) and dried in vacuo. The trisodium salt of 1,1′,5,5′-tetrahydro-4-hydroxy-2,2′-dioxo-[3,4′-bi-2H-pyrrole]-1,1′-diacetic acid is obtained in the form of white microcrystals; melting point>300° (decomposition).

EXAMPLE 18

Analogously to the procedure described in Example 1, from 25.7 g (0.1 mol) of 3-ethoxycarbonyl-2,5-hydro-4-hydroxy-1H-pyrrole-1-acetic acid ethyl ester there is obtained, by treatment in water and acetonitrile, 1,1′,5,5′-tetrahydro-4-hydroxy-2,2′-dioxo-[3,4′-bi-2H-pyrrole]-1,1′-diacetic acid diethyl ester in the form of pale yellow crystals having a melting point of 192°-194°.

This can be converted into 1,1′,5,5′-tetrahydro-4-hydroxy-2,2′-dioxo-[3,4′-bi-2H-pyrrole]-1,1′-diacetic acid diamide having a melting point of 298°-300° (decomposition) in a manner analogous to that described in Example 1 or into 1,1′,5,5′-tetrahydro-4-hydroxy-2,2′-dioxo-[3,4′-bi-2H-pyrrole]-1,1′-diacetic acid having a melting point of 268° (decomposition) in a manner analogous to that described in Example 3.

EXAMPLE 19

Analogously to the procedure described in Example 1, from 7.7 g (0.022 mol) of 1,1′,5,5′-tetrahydro-4-hydroxy-2,2′-dioxo-[3,4′-bi-2H-pyrrole]-1,1′-di-(3-propionic acid) dimethyl ester there is obtained, by treatment in 70 ml of concentrated aqueous ammonia solution, 1,1′,5,5′-tetrahydro-4-hydroxy-2,2′-dioxo-[3,4′-bi-2H-pyrrole]-1,1′-di-(3-propionic acid)-diamide in the form of white crystals having a melting point of 230° (decomposition).

The 1,1′,5,5′-tetrahydro-4-hydroxy-2,2′-dioxo-[3,4′-bi-2H-pyrrole]-1,1′-di-(3-propionic acid) dimethyl ester used as starting material can, likewise analogously to the procedure described in Example 1, be manufactured as follows:

(a) of N-(2-cyanoethyl)-glycine are suspended in 550 ml of methanol and cooled to 5° in an ice/water bath. At this temperature, while cooling, a current of hydrogen chloride is passed into the reaction mixture for a period of 3 hours. The reaction mixture is then stirred at room temperature for 12 hours and then heated under reflux for a further 1 hour. The colourless suspension is concentrated to approximately ⅔ and filtered, the residue is then washed with a small quantity of cold methanol, and the filtrate is neutralised with sodium bicarbonate and concentrated to dryness by evaporation The oily residue is taken up in 250 ml of chloroform and extracted by shaking with water. The organic phase is dried over magnesium sulphate, concentrated to dryness by evaporation and the resulting residue is distilled under greatly reduced pressure N-(methoxycarbonylmethyl)-β-aminopropionic acid methyl ester is obtained in the form of a colourless oil; boiling point 73°-75° (0.005 mm Hg=6.25×10$^{-6}$ bar).

(b) Analogously to the procedure described in Example 1(a), from 35.0 g (0.2 mol) of N-(methoxycarbonylmethyl)-β-aminopropionic acid methyl ester, 33 ml (0.24 mol) of triethylamine and 36.2 g (0.24 mol) of malonic acid monomethyl ester chloride in 60 ml of methylene chloride there is obtained N-methoxycarbonylacetyl-N-methoxycarbonylmethyl-β-aminopropionic acid methyl ester in the form of a yellowish oil.

(c) Analogously to the procedure described in Example 1(b), from 53.2 g (0.19 mol) of N-methoxycarbonylacetyl-N-methoxycarbonylmethyl-β-aminopropionic acid methyl ester in 55 ml of methanol and 4.4 g of sodium in 240 ml of methanol there is obtained 3-[2,5-dihydro-4-hydroxy-3-methoxycarbonyl-2-oxo-1H-pyrrole]-propionic acid methyl ester having a melting point of 170°-171°.

(d) Analogously to the procedure described in Example 1(c), from 24.3 g (0.1 mol) of the above-described pyrrole derivative in 24 ml of water and 240 ml of acetonitrile there is obtained 1,1′,5,5′-tetrahydro-4-hydroxy-2,2′-dioxo-[3,4′-bi-2H-pyrrole]-1,1′-di-(3propionic acid) dimethyl ester in the form of white crystals having a melting point of 183°-184°.

EXAMPLE 20

Analogously to the procedure described in Example 3, from 7.8 g (0.022 mol) of 1,1′,5,5′-tetrahydro-4-hydroxy-2,2′-dioxo-[3,4′-bi-2H-pyrrole]-1,1′-di-(3-propionic acid) dimethyl ester in 100 ml of water and 20 ml of concentrated aqueous sodium hydroxide solution there is obtained 1,1′,5,5′-tetrahydro-4-hydroxy-2,2′-dioxo-[3,4′-bi-2H-pyrrole]-1,1′-di-(3-propionic acid) in the form of colourless crystals having a melting point of 227° (decomposition).

EXAMPLE 21

4.4 g (0.015 mol) of 1,1′,5,5′-tetrahydro-4-hydroxy-2,2′-dioxo-[3,4′-bi-2H-pyrrole]-1,1′-diacetic acid are suspended together with 3.3 g (0.030 mol) of glycinamide hydrochloride in 80 ml of dimethylformamide. Then, at room temperature, first 6.8 ml (0.05 mol) of triethylamine and then 8.1 ml (0.03 mol) of triphenyl phosphite are added dropwise thereto; the resulting slightly yellow suspension of low viscosity is stirred for 3 hours at 85°-90°. The resulting brown solution is cooled to 5° and 160 ml of diethyl ether are added. The precipitate formed is filtered off, washed with diethyl ether, suspended in 80 ml of ethanol and acidified with an excess of an approximately 4N hydrochloric acid solution in diethyl ether. After stirring thoroughly, filtration is again carried out and the filtration residue is stirred with 90 ml of water and 9 ml of 4N hydrochloric acid for 12 hours at room temperature. The suspension is filtered and the filtration residue is washed with water and acetone and dried at 60° under a high vacuum. 1,1′,5,5′-tetrahydro-4-hydroxy-2,2′-dioxo-[3,4′-bi-2H-pyrrole]-1,1′-diacetic acid di-N-(carbamoylmethyl)amide is obtained in the form of white crystals having a melting point of 215° (decomposition).

EXAMPLE 22

Analogously to the procedure described in Example 21, from 4.4 g (0.015 mol) of 1,1′,5,5′-tetrahydro-4-hydroxy-2,2′-dioxo-[3,4′-bi-2H-pyrrole]-1,1′-diacetic acid, 6.6 g (0.03 mol) of 1,2,5,6-tetrahydropyridine-3-carboxylic acid methyl ester hydrobromide, 6.8 ml of triethylamine and 9.3 g of triphenyl phosphite in 80 ml of dimethylformamide there is obtained 1,1',5,5'-tetrahydro-4-hydroxy-1,1'-di-(3-methoxycarbonyl-1,2,3,6-tetrahydropyridinocarbonylmethyl)-[3,4'-bi-2H-pyrrole]-2,2'-dione in the form of white crystals; melting point 208° (decomposition).

EXAMPLE 23

Analogously to the procedure described in Example 21, from 3.3 g (0.011 mol) of 1,1',5,5'-tetrahydro-4-hydroxy-2,2'-dioxo-[3,4'-bi-2H-pyrrole]-1,1'-diacetic acid, 4.1 g of adamantylamine hydrochloride (0.022 mol), 5.1 ml of triethylamine and 6.8 g of triphenyl phosphite in 80 ml of dimethylformamide there is obtained 1,1',5,5'-tetrahydro-4-hydroxy-2,2'-dioxo-[3,4'-bi-2H-pyrrole]-1,1'-diacetic acid di-N-adamantylamide in the form of white crystals having a melting point of 220° (decomposition).

EXAMPLE 24

Analogously to the procedure described in Example 21, from 3.8 g (0.013 mol) of 1,1',5,5'-tetrahydro-4-hydroxy-2,2'-dioxo-[3,4'-bi-2H-pyrrole]-1,1'-diacetic acid, 3.3 g (0.026 mol) of N-acetylpiperazine, 1.8 ml of triethylamine and 8.1 g of triphenyl phosphite in 80 ml of dimethylformamide there is obtained 1,1',5,5'-tetrahydro-4-hydroxy-2,2'-dioxo-[3,4'-bi-2H-pyrrole]-1,1'-diacetic acid di-(4-acetyl)-piperazide in the form of white crystals having a melting point of 220° (decomposition).

EXAMPLE 25

Analogously to the procedure described in Example 21, from 4.5 g (0.015 mol) of 1,1',5,5'-tetrahydro-4-hydroxy-2,2'-dioxo-[3,4'-bi-2H-pyrrole]-1,1'-diacetic acid, 5.0 g (0.05 mol) of N-methylpiperazine and 9.3 g of triphenyl phosphite in 80 ml of dimethylformamide there is obtained 1,1',5,5'-tetrahydro-4-hydroxy-2,2'-dioxo-[3,4'-bi-2H-pyrrole]-1,1'-diacetic acid di-(4-methyl)-piperazide dihydrochloride in the form of white crystals having a melting point of 263° (decomposition).

EXAMPLE 26

3.0 g (0.010 mol) of 1,1',5,5'-tetrahydro-4-hydroxy-2,2'-dioxo-[3,4'-bi-2H-pyrrole]-1,1'-diacetic acid diamide are suspended in 70 ml of methanol; 2.4 g of tris-(hydroxymethyl)-aminomethane are added and the whole is stirred at room temperature for 12 hours, during which time the free acid goes into solution and precipitates again in the form of a salt. The resulting precipitate is filtered off, washed with cold methanol and dried under greatly reduced pressure at 60°. The tris-(hydroxymethyl)-methylammonium salt of 1,1',5,5'-tetrahydro-4-hydroxy-2,2'-dioxo-[3,4'-bi-2H-pyrrole]-1,1'-diacetic acid diamide is obtained in the form of white crystals having a melting point of 203° (decomposition).

EXAMPLE 27

4.9 g (0.015 mol) of 1,1',5,5'-tetrahydro-4-hydroxy-2,2'-dioxo-[3,4'-bi-2H-pyrrole]-1,1'-diacetic acid dimethyl ester are stirred in 40 ml of a 70% aqueous solution of 2-diisopropylaminoethylamine for 3 days at room temperature. The oily residue that is obtained after concentration by evaporation under a high vacuum is dissolved in 100 ml of acetone, and 6 ml of a 30% solution of sodium methoxide in methanol are added. The resulting product is filtered off, washed with acetone and dried at 70° under greatly reduced pressure. The sodium salt of 1,1',5,5'-tetrahydro-4-hydroxy-2,2'-dioxo-[3,4'-bi-2H-pyrrole]-1,1'-diacetic acid di-N-(2-diisopropylaminoethyl)-amide is obtained in the form of a pale yellowish-brown powder; melting point 215° (decomposition).

EXAMPLE 28

4.3 g of 2,5-dihydro-4-hydroxy-3-methoxycarbonyl-2-oxo-1H-pyrrole-1-acetamide are suspended in 50 ml of acetonitrile and 30 ml of water. Heating to 75° initiates the removal of carbon dioxide; the reaction mixture is stirred at this temperature for 12 hours. After cooling, the resulting product is filtered off, washed with water and acetone and dried under reduced pressure. 1,1',5,5'-tetrahydro-4-hydroxy-2,2'-dioxo-[3,4'-bi-2H-pyrrole]-1,1'-diacetic acid diamide is obtained in the form of white crystals having a melting point of 300° (decomposition). The product is identical to that described in Example 1.

The starting material can be manufactured, for example, as follows:

23 g (0.1 mol) of the 2,5-dihydro-4-hydroxy-3-methoxycarbonyl-2-oxo-1H-pyrrole-1-acetic acid methyl ester described in Example 1 are dissolved in 200 ml of a concentrated aqueous ammonia solution and stirred at room temperature for 12 hours. The yellowish solution is then concentrated to dryness by evaporation under a water-jet vacuum. The resulting solid residue is dissolved in 200 ml of water, and a concentrated aqueous solution of hydrochloric acid is added until a strongly acidic reaction takes place. The resulting colourless precipitate is filtered off, washed with water and acetone and dried at 50° under reduced pressure. 2,5-dihydro-4-hydroxy-3-methoxycarbonyl-2-oxo-1H-pyrrole-1-acetamide is obtained in the form of white crystals having a melting point of 202° (decomposition).

EXAMPLE 29

3.2 g (0.01 mol) of 1,1',5,5'-tetrahydro-4-hydroxy-2,2'-dioxo-[3,4'-bi-2H-pyrrole]-1,1'-diacetic acid diamide in 60 ml of methanol are hydrogenated in the presence of 0.3 g of platinum oxide at room temperature and under normal pressure. After the theoretical amount of hydrogen has been absorbed the hydrogenation ceases and the catalyst is removed by filtration from the resulting reaction mixture which is then concentrated to dryness by evaporation and the resulting residue is boiled up briefly in 40 ml of ethanol, filtered and the filtrate is again concentrated to dryness by evaporation. Octahydro-4-hydroxy-2,2'-dioxo-[3,4'-bi-2H-pyrrole]-diacetic acid diamide is obtained in the form of a colourless amorphous powder having a melting point upwards from ~120° (decomposition).

EXAMPLE 30

Analogously to the procedure described in Example 29, from 6 g (0.02 mol) of 1,1',5,5'-tetrahydro-4-hydroxy-2,2'-dioxo-[3,4'-bi-2H-pyrrole]-1,1'-diacetic acid there is obtained octahydro-4-hydroxy-2,2'-dioxo-[3,4'-bi-2H-pyrrole]-1,1'-diacetic acid in the form of a colourless amorphous powder.

EXAMPLE 31

In a manner analogous to that described in Examples 1 to 28 it is also possible to manufacture:

1,1′,5,5′-tetrahydro-4-hydroxy-2,2′-dioxo-[3,4′-bi-2H-pyrrole]-1,1′-diacetic acid di-(cis-2,6-dimethyl)piperazide, 1,1′,5,5′-tetrahydro-4-hydroxy-2,2′-dioxo-[3,4′-bi-2H-pyrrole]-1,1′-diacetic acid di-(2-tetramethylene)-piperidide, 1,1′,5,5′-tetrahydro-4-hydroxy-2,2′-dioxo-[3,4′-bi-2H-pyrrole]-1,1′-diacetic acid di-(3-methoxycarbonyl-4-oxo)-piperidide, and 1,1′,5,5′-tetrahydro-4-hydroxy-5,5′-di-(tetramethylene)-2,2′-dioxo-[3,4′-bi-2H-pyrrole]-1,1′-diacetic acid diamide.

EXAMPLE 32

Tablets containing 25 mg of active ingredient, for example 1,1′,5,5′-tetrahydro-4-hydroxy-2,2′-dioxo-[3,4′-bi-2H-pyrrole]-1,1′-diacetic acid diamide or a salt, for example the sodium salt, thereof, can be manufactured as follows:

| Constituents (for 1000 tablets): | |
|---|---|
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Manufacture:

All the solid ingredients are first forced through a sieve of 0.6 mm mesh width. Then the active ingredient, the lactose, the talc, the magnesium stearate and half the starch are mixed together. The other half of the starch is suspended in 40 ml of water and this suspension is added to a boiling solution of the polyethylene glycol in 100 ml of water and the mixture is granulated, if necessary with the addition of water. The granulate is dried overnight at 35° forced through a sieve of 1.2 mm mesh width and compressed to form tablets of approximately 6 mm diameter that are concave on both sides.

EXAMPLE 33

Tablets containing 10 mg of active ingredient, for example 1,1′,5,5′-tetrahydro-4-hydroxy-2,2′-dioxo-3,4′-bi-2H-pyrrole]-1,1′-diacetic acid diamide or a salt, for example the sodium salt, thereof, can be manufactured as follows:

| Constituents (for 1000 tablets): | |
|---|---|
| active ingredient | 10.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Manufacture:

All the solid ingredients are first forced through a sieve of 0.6 mm mesh width. Then the active ingredient, the lactose, the talc, the magnesium stearate and half the starch are mixed together. The other half of the starch is suspended in 40 ml of water and this suspension is added to a boiling solution of the polyethylene glycol in 1000 ml of water and the mixture is granulated, if necessary woth the addition of water. The granulate is dried overnight at 35° forced through a sieve of 1.2 mm mesh width and compressed to form tablets of approximately 6 mm diameter that are concave on both sides.

EXAMPLE 34

Tablets containing 5 mg of active ingredient, for example 1,1′,5,5′-tetrahydro-4-hydroxy-2,2′-dioxo-[3,4′-bi-2H-pyrrole]-1,1′-diacetic acid diamide or a salt, for example the sodium salt, thereof, can be manufactured as follows:

| Constituents (for 1000 tablets): | |
|---|---|
| active ingredient | 5.0 g |
| lactose | 150.7 g |
| wheat starch | 27.5 g |
| polyethylene glycol 6000 | 5.0 g |
| talc | 5.0 g |
| magnesium stearate | 1.8 g |
| demineralised water | q.s. |

Manufacture:

All the solid ingredients are first forced through a sieve of 0.6 mm mesh width. Then the active ingredient, the lactose, the talc, the magnesium stearate and half the starch are mixed together. The other half of the starch is suspended in 40 ml of water and this suspension is added to a boiling solution of the polyethylene glycol in 100 ml of water and the mixture is granulated, if necessary with the addition of water. The granulate is dried overnight at 35° forced through a sieve of 1.2 mm mesh width and compressed to form tablets of approximately 6 mm diameter that are concave on both sides.

EXAMPLE 35

In a manner analogous to that described in Examples 32 to 34 it is also possible to manufacture pharmaceutical preparations containing a different compound of the formula I according to Examples 1 to 31 or a salt thereof.

I claim:

1. A compound selected from the group consisting of (3,4′-bi-2H-pyrrole)-2,2′-diones of the formula

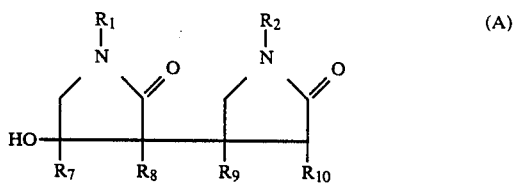

(A)

wherein $R_1$ and $R_2$ are identical and each represents $Y-C(O)C_{1-4}$—alkyl wherein Y is (1) pyrrolidino or piperidino which is unsubstituted or 3-substituted by $C_{1-4}$—alkoxy carbonyl and 4-substituted by hydroxy or oxo;

(2) 2,5-dihydropyrrolo or 1,2,3,6-tetrahydropyridino which is (a) 3-substituted by $C_{1-4}$—alkoxycarbonyl and (b) 4-unsubstituted or 4-substituted by hydroxy; or (3) piperazino which is unsubstituted or N′-substituted by $C_{1-4}$ alkanoyl or $C_{1-4}$ alkyl, or is morpholino or is thiomorpholino; and $R_7$ to $R_{10}$ are all hydrogen or $R_7$ together with $R_8$ and $R_9$ together with $R_{10}$ represent an additional bond, or a pharmaceutically acceptable salt thereof.

2. Compounds according to claim 1 in which $R_7$ together with $R_8$ and $R_9$ together with $R_{10}$ represent in each case an additional bond.

3. A compound as claimed in claim 1 being 1,1',5,5'-tetrahydro-4-hydroxy-2,2'-dioxo-[3,4'-bi-2-H-pyrrole]-1,1'-diacetic acid di-(4-methyl)-piperazide or a pharmaceutical acceptable salt thereof.

4. The sodium, potassium, ammonium, diethylammonium, bis-(2-hydroxyethyl)ammonium, tris-(2-hydroxyethyl)-ammonium, tris-(hydroxymethyl)methylammonium or N,N-dimethyl-N-(2-hydroxyethyl)ammonium salt of a compound according to claim 1.

5. Pharmaeutical preparations containing a compound according to claim 1 in free form or in the form of a pharmaceutically acceptable salt in addition to pharmaceutical adjuncts.

6. A method of treatment of cerebral insufficiencies characterised in that a therapeutically effective amount of a compound as claimed in claim 1 is administrated to a warm-blooded organism in need of such treatment.

7. The compound of claim 1 wherein $R_1$ and $R_2$ are the same and represent $N'$-$C_{1-4}$ alkylpiperazinocarbonylmethyl or a pharmaceutically acceptable salt thereof.

8. 1,1',5,5'-tetrahydro-4-hydroxy-1,1'-di-(3-methoxycarbonyl-1,2,3,6-tetrahydrophridinocarbonylmethyl)-[3,4'-bi-2-H-pyrrole]-2,2'-dione; or a pharmaceutically acceptable salt therof according to claim 1.

9. 1,1',5,5'-tetrahydro-4-hydroxy-2,2'-dioxo-[3,4'-bi-2-H-pyrrole]-1,1'-diacetic acid di-(4-methyl)-piperazide dihydrochloride according to claim 1.

10. The compound of claim 1 which is 1,1',5,5'-tetrahydro-4-hydroxy-2,2'-dioxo-[3,4'-bi-2-H-pyrrole]-1,1'-diacetic acid di-(4-acetyl)-piperazide.

11. The compound of claim 1 which is 1,1',5,5'-tetrahydro-4-hydroxy-2,2'-dioxo-[3,4'-bi-2-H-pyrrole]-1,1'-diacetic acid dimorpholide.

12. The compound of claim 1 which is 1,1',5,5'-tetrahydro-4-hydroxy-2,2'-dioxo-[3,4'-bi-2-H-pyrrole]-1,1'-diacetic acid dipiperidide.

* * * * *